US012721295B2

(12) United States Patent
Graham et al.

(10) Patent No.: US 12,721,295 B2
(45) Date of Patent: Sep. 1, 2026

(54) PAPAVER SOMNIFERUM PLANTS WITH A MODIFIED TRANSCRIPTION FACTOR GENE IN THE REGULATION OF BENZYLISOQUINOLINE ALKALOIDS SYNTHESIS

(71) Applicant: Sun Pharmaceutical Industries Australia Pty Limited, Notting Hill (AU)

(72) Inventors: Ian Graham, York (GB); Thilo Winzer, York (GB); Yi Li, York (GB)

(73) Assignee: Sun Pharmaceutical Industries Australia Pty Limited, Notting Hill (AU)

( * ) Notice: Subject to any disclaimer, the term of this patent is extended or adjusted under 35 U.S.C. 154(b) by 134 days.

(21) Appl. No.: 18/563,183

(22) PCT Filed: May 24, 2022

(86) PCT No.: PCT/IB2022/054862

§ 371 (c)(1),
(2) Date: Nov. 21, 2023

(87) PCT Pub. No.: WO2022/249068

PCT Pub. Date: Dec. 1, 2022

(65) Prior Publication Data

US 2024/0240194 A1 Jul. 18, 2024

(30) Foreign Application Priority Data

May 25, 2021 (GB) ...................................... 2107438

(51) Int. Cl.
*A01H 6/64* (2018.01)

(52) U.S. Cl.
CPC ......... *A01H 6/64* (2018.05); *C12N 2830/002* (2013.01)

(58) Field of Classification Search
None
See application file for complete search history.

(56) References Cited

FOREIGN PATENT DOCUMENTS

| | | | |
|---|---|---|---|
| GB | 2583024 | | 10/2020 |
| JP | 2006149333 A | * | 6/2006 |
| WO | WO 2009/143574 | | 12/2009 |
| WO | WO 2018/039749 | | 3/2018 |

OTHER PUBLICATIONS

Guo L et al., "The opium poppy genome and morphinan production.", Science, Oct. 19, 2018;362(6412):343-347 (Year: 2018).*

Li et al. (Genome-wide analysis of bHLH transcription factor family reveals their involvement in kernel development and biotic stress responses in Chinese chestnut. Sep. 18, 2025. Frontiers in plant science vol. 16 1627760, doi:10.3389/fpls.2025.1627760. (Year: 2025).*

Das et al., (Variation of gene expression in plants is influenced by gene architecture and structural properties of promoters. 2019. PLoS ONE 14(3): e0212678 (Year: 2019).*

Yamada et al. (CjbHLH1 homologs regulate sanguinarine biosynthesis in Eschscholzia californica cells. 2015. Plant & cell physiology vol. 56,5: 1019-30. doi:10.1093/pcp/pcv027 (Year: 2015).*

Yamada et al. (Isoquinoline alkaloid biosynthesis is regulated by a unique bHLH-type transcription factor in Coptis japonica. 2011. Plant & cell physiology vol. 52,7: 1131-41. doi: 10.1093/pcp/pcr062 (Year: 2011).*

National Center for Biotechnology Information (NCBI) (AB564544, 2010 (V)), (Year: 2010).*

UniProt (A0A4Y7KW09_PAPSO 2010) (Year: 2010).*

GENBANK Accession No. A0A4Y7KW09_PAPSO, BHLH domain-containing protein, Apr. 7, 2021.

International Search Report and Written Opinion dated Jul. 11, 2022, issued for PCT/IB2022/054862 (11 pages).

Search Report dated Nov. 25, 2021, issued for GB 2107438.0 (1 page.

Yamada et al., "Transcription factors in alkaloid biosynthesis," *Int. Rev. Cell Mol. Biol.* 305:339-382, 2013.

Yamada et al., "CjbHLH1 homologs regulate sanguinarine biosynthesis in *Eschscholzia californica* cells," *Plant Cell Physiol*, 56(5):1019-1030, 2015.

Eshaghi et al., "Network-based identification of hub transcription factors associated with benzylisoquinoline alkaloid biosynthesis in *Papaver somniferum," Biochemistry and Biophysics Reports*, 43:102147, 2025 (including supplemental materials; 84 pages).

EMBL Accession No. CM010723.1, Papaver somniferum (opium poppy) hypothetical protein, Jun. 24, 2019.

* cited by examiner

*Primary Examiner* — Phuong T Bui
*Assistant Examiner* — Christian Jose Ordaz
(74) *Attorney, Agent, or Firm* — Klarquist Sparkman, LLP

(57) ABSTRACT

Transcription cassettes and vectors comprising a nucleotide sequence encoding a transcription factor; plants, plant cells, plant cell cultures and seeds that are genetically engineered to include a recombinant copy or copies of the nucleic acid encoding the transcription factor; and processes for the extraction of benzylisoquinoline alkaloids from the genetically engineered plants are provided. Plants carrying a mutated genomic copy of said transcription factor and its effect on benzylisoquinoline alkaloids synthesis are also provided.

6 Claims, 6 Drawing Sheets

Figure 3:
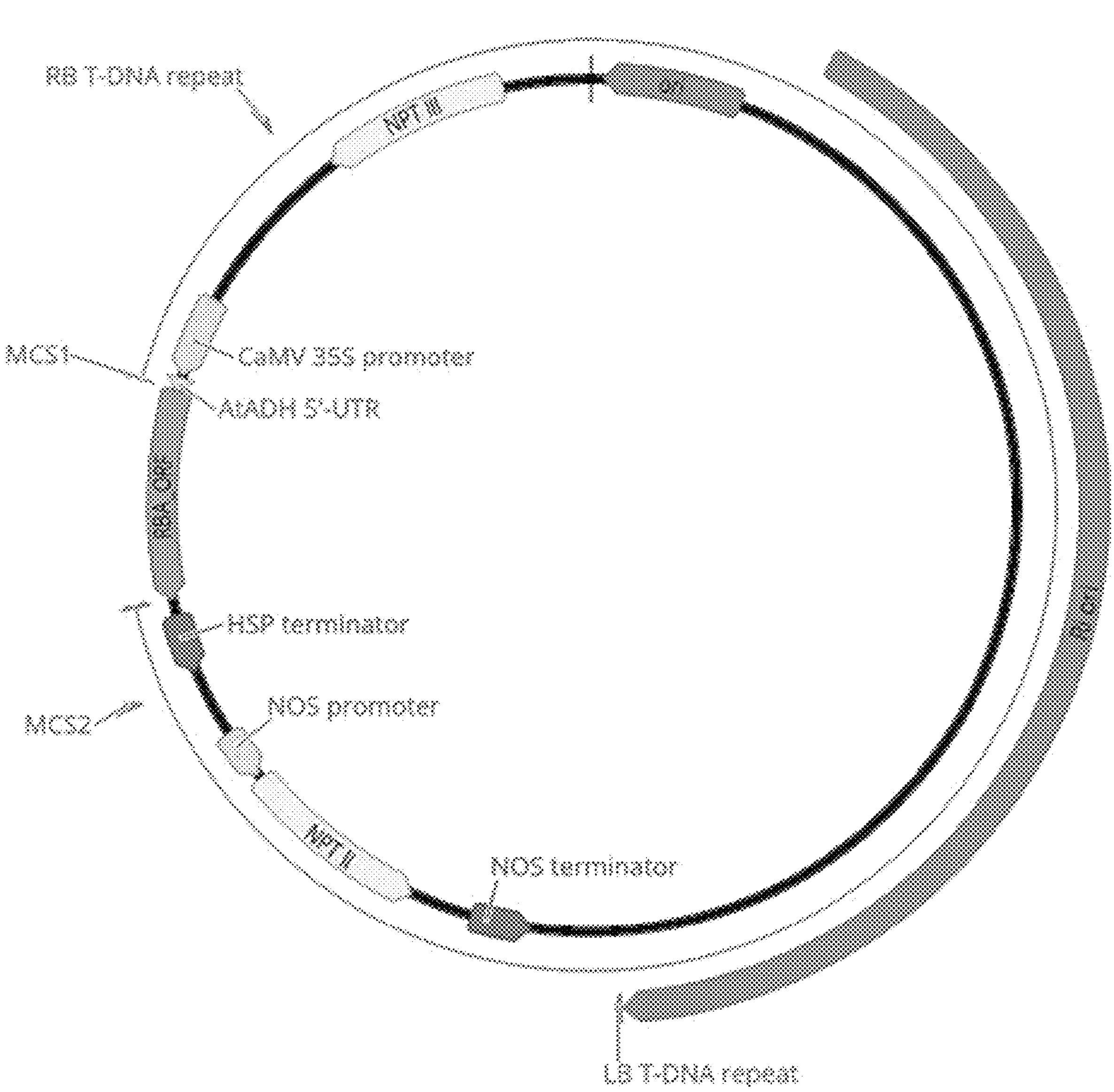

Specification includes a Sequence Listing.

Figure 1
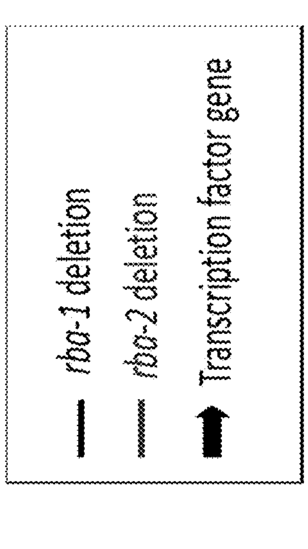
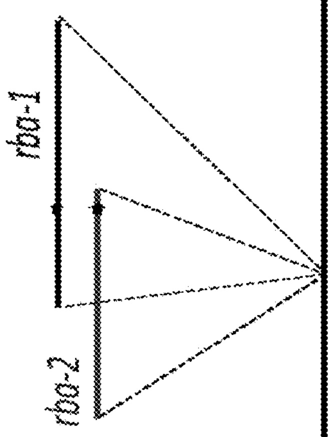
Chromosome 9

Figure 2

Sequences PS0917990 (*RBA*) coding sequence from HN1 reference genome

ATGATCAGTAGTTATTCTAAGAGTACTGACGCAGAAGTATCGAAGAAATC
GAGGAAAAACACACCAGCATCATCATCATCATCCATGGCAATTGACTGGA
GTAGTAGTGATTGGGAAGGAAAATCAGGATCACAAGGAGGAGTAGGAGGA
AATGGAGGTGGAGTTGATGCTAGAGAAAGACATAAACTAGCAGAAAGAGA
AAGAAGAAAATCAATGAGAGAATTATTTCTATCTCTTCACTCGCTATTAC
CTCATTCCAATACGGTGCGTAAAGAACAATCAGCAATTCTCGATGAAATT
ATCAAATATATACCGATTGCTGCTGCTCGTCTTCGTTCACTTCAGAATCG
TAAGGAAAGTAGCAGTAATAATTCATCTAATCATTCTTCATTGACTTCAT
CTGCATCTTCATCGAAAGTATCTTCGACCGTGCTTTCAAAAACAAAATCA
TATTCTTCAGTACCATCGGTTCAAGTCTCAGATCGTGATAACAAGAATAA
CAATAGTAAAAACTCAGCTACTTCTGCTGTGGCTAATACGATCATTGACT
GTGACATCCGGGTTGCTCCTGAACCTTCATCTTCTGTGGCGATTCGCATT
AGAGGTGACCGGGTGAATGTTTCTTTAAGTGATTCTAAGGGTACTTCACA
CACTCTGTTATTATCTGCTGTTTTAGATGAGCTTGAAAATCATCAACTTG
AACTTGTTCGTTCTACTCATTGTCGCGATGGAAGTAAAGTCTTGCATCAT
TCCGAAAGCAAGATTTGTGATGGACTGGATAAATCTCCCAATTTGTTGAA
GTCGAGATTACAGGACTTGGCAAGAAAACTTCACAAATTGAGGAAATCGA
CTTCACTCAAGAGAACATTCGATCAAATTGAATGA (SEQ ID NO 1)

MISSYSKSTDAEVSKKSRKNTPASSSSSMAIDWSSSDWEGKSGSQGGVGG
NGGGVDARERHKLAERERRKSMRELFLSLHSLLPHSNTVRKEQSAILDEI
IKYIPIAAARLRSLQNRKESSSNNSSNHSSLTSSASSSKVSSTVLSKTKS
YSSVPSVQVSDRDNKNNNSKNSATSAVANTIIDCDIRVAPEPSSSVAIRI
RGDRVNVSLSDSKGTSHTLLLSAVLDELENHQLELVRSTHCRDGSKVLHH
SESKICDGLDKSPNLLKSRLQDLARKLHKLRKSTSLKRTFDQIE (SEQ ID NO 2)

Figure 2 (continued)

PS0917990 (*RBA*) coding sequence including 5' UTR and 3' UTR from RNAseq

GTAGTGGAGTGGTAGTTGCAGTTGATTCAAAGAGATTACTGTGTCGGTCCAT
AAGACCAATCTTCTTTCATCCTCCATGATCAGTAGTTATTCTAAGAGTACTG
ACGCAGAAGTATCGAAGAAATCGAGGAAAAACACACCAGCATCATCATCATC
ATCCATGGCAATTGACTGGAGTAGTAGTGATTGGGAAGGAAAATCAGGATCA
CAAGGAGGAGTAGGAGGAAATGGAGGTGGAGTTGATGCTAGAGAAAGACATA
AACTAGCAGAAAGAGAAAGAAGAAAATCAATGAGAGAATTATTTCTATCTCT
TCACTCGCTATTACCTCATTCCAATACGGTGCGTAAAGAACAATCAGCAATT
CTCGATGAAATTATCAAATATATACCGATTGCTGCTGCTCGTCTTCGTTCAC
TTCAGAATCGTAAGGAAAGTAGCAGTAATAATTCATCTAATCATTCTTCATT
GACTTCATCTGCATCTTCATCGAAAGTATCTTCGACCGTGCTTTCAAAAACA
AAATCATATTCTTCAGTACCATCGGTTCAAGTCTCAGATCGTGATAACAAGA
ATAACAATAGTAAAAACTCAGCTACTTCTGCTGTGGCTAATACGATCATTGA
CTGTGACATCCGGGTTGCTCCTGAACCTTCATCTTCTGTGGCGATTCGCATT
AGAGGTGACCGGGTGAATGTTTCTTTAAGTGATTCTAAGGGTACTTCACACA
CTCTGTTATTATCTGCTGTTTTAGATGAGCTTGAAAATCATCAACTTGAACT
TGTTCGTTCTACTCATTGTCGCGATGGAAGTAAAGTCTTGCATCATTCCGAA
AGCAAGATTTGTGATGGACTGGATAAATCTCCCAATTTGTTGAAGTCGAGAT
TACAGGACTTGGCAAGAAAACTTCACAAATTGAGGAAATCGACTTCACTCAA
GAGAACATTCGATCAAATTGAATGATTTGGTTTATTAGTTTTATTAATTACT
TAAATTTTAGTGGTTATAGTAGCGGAGGAAACAGAGTGATTGTACAAATGAA
ATGAGTGGTTGAAGGATCCCAGCTCTGTGTCTTGTTCGTAATAATAATAAAT
AAACTAATCTCCACGTTTTCCCTACCAAACCTACTCAAATCTCAAAATATAC
ACTCTTCTCTTTCCTTCATGGCACTTTCTACTATTTCATTATTGCTCATGTG
CAAAACGATGATCGTATAACACCAAAGCGATCTTCTCTTTCCTTTACACTAC
AGTAGTTGCTTTCTGTATCCAAAATCTGCCAC (SEQ ID NO: 3)

Figure 2 (continued)

PS0917990 (*RBA*) genomic sequence including 5'UTR and 3' UTR from HN1 reference genome GTAGTGGAGTGGTAGTTGCAGTTGATTCAAAGAGATTACTGTGTCGGTCCATAAGAC
CAATCTTCTTTCATCCTCCATGATCAGTAGTTATTCTAAGAGTACTGACGCAGAAGT
ATCGAAGAAATCGAGGAAAAACACACCAGCATCATCATCATCATCCATGGCAATTGA
CTGGAGTAGTAGTGATTGGGAAGGAAAATCAGGATCACAAGGAGGAGTAGGAGGAAA
TGGAGGTGGAGTTGATGCTAGAGAAAGACATAAACTAGCAGAAAGAGAAAGAAGAAA
ATCAATGAGAGAATTATTTCTATCTCTTCACTCGCTATTACCTCATTCCAATACGGT
GCGTAAAGAACAATCAGCAATTCTCGATGAAATTATCAAATATATACCGATTGCTGC
TGCTCGTCTTCGTTCACTTCAGAATCGTAAGGAAAGTAGCAGTAATAATTCATCTAA
TCATTCTTCATTGACTTCATCTGCATCTTCATCGAAAGTATCTTCGACCGTGCTTTC
AAAAACAAAATCATATTCTTCAGTACCATCGGTTCAAGTCTCAGATCGTGATAACAA
GAATAACAATAGTAAAAACTCAGCTACTTCTGCTGTGGCTAATACGATCATTGACTG
TGACATCCGGGTTGCTCCTGAACCTTCATCTTCTGTGGCGATTCGCATTAGAGGTGA
CCGGGTGAATGTTTCTTTAAGTGATTCTAAGGGTACTTCACACACTCTGTTATTATC
TGCTGTTTTAGATGAGCTTGAAAATCATCAACTTGAACTTGTTCGTTCTACTCATTG
TCGCGATGGAAGTAAAGTCTTGCATCATTCCGAAAGCAAGGTTTGTTTCTTAATTTC
TTTTTTCTTTAATGATCCGTGATTCGCTTTTGTTTTTTGAATGATTTGTTTTTTAAT
TATTACTTTATCAATGATATCAGCTCTGATTCTGAGTATCTTCTAGTATATGTATAT
TGTGTACTTGCTGAATCGGGAATGTGATTATTCTATTGCTAGAGATCTGTGTTCTGC
TGTAGACTCACGATCTAGCTTTCAGAATCATGTGTCAAATCTTTGAATTTCAGTTCA
CATAAAATTTTAGTTGGGATAGTTTTCTTCGCTTTTGAAGATCCCGATTCTCTTTTA
TCTGACACATTATTCATTTTGTTAATGCGTTTTAGGTATCATTATTAGTTTTAATTA
TTATTATCTAACTAGACATGTTTTTTCTTTTGGCAGATTTGTGATGGACTGGATAAA
TCTCCCAATTTGTTGAAGTCGAGATTACAGGACTTGGCAAGAAAACTTCACAAATTG
AGGAAATCGACTTCACTCAAGAGAACATTCGATCAAATTGAATGATTTGGTTTATTA
GTTTTATTAATTACTTAAATTTTAGTGGTTATAGTAGCGGAGGAAACAGAGTGATTG
TACAAATGAAATGAGTGGTTGAAGGATCCCAGCTCTGTGTCTTGTTCGTAATAATAA
TAAATAAACTAATCTCCACGTTTTCCCTACCAAACCTACTCAAATCTCAAAATATAC
ACTCTTCTCTTTCCTTCATGGCACTTTCTACTATTTCATTATTGCTCATGTGCAAAA
CGATGATCGTATAACACCAAAGCGATCTTCTCTTTCCTTTACACTACAGTAGTTGCT
TTCTGTATCCAAAATCTGCCACCAACATTTGTCCCCGAAATGCGTTAATTACCCGTT
CATCACACATAGTTTCGTGTGGGATGCTCTAAAAAAGAATCGTCACTTTTAGATCTG
TGATTTAGACGGATACAGTAAATTATGTGGTTACTGTGGTTATAATAGTGTTGCTTT
GTGTAGATTTGGTACACCTTCGTATAATTTGGTCATTTGGTGTTCATGTAACAATCT
TTCAGAAACATCTATTCATGATTCACTCATTCATACAAAGAAATTAGTAGCCTTGAT
CTTCAACAGGCCAGTGGATGAGTTTTAGAAACTTTAAAGAAAACAAGGATATACTAC
AAAGAAAGATTATTTTATTTCTTAAATAATTTTAGAAAGAAGAAATCATGGGGTGGA
CGTCTTAATCAAGAGAAAGTTGAGGTGACTCCACTAAGTGAGATGAAAGTTGGATGT
AAACGTG (SEQ ID NO: 4)

Figure 2 (continued)

PS0917990 (*RBA*) sequence including part of the 5'UTR and 3' UTR from a sequenced cDNA clone of HN4

GAAGGTGTAGTGGAGTGGTAGTTGCAGTTGATTCAAAGAGATTACTG
TGTCGGTCCATAAGACCAATCTTCTTTCATCCTCCATGATCAGTAGT
TATTCTAAGAGTACTGACGCAGAAGTATCGAAGAAATCGAGGAAAAA
CACACCAGCATCATCATCATCATCCATGGCAATTGACTGGAGTAGTA
GTGATTGGGAAGGAAAATCAGGATCACAAGGAGGAGTAGGAGGAAAT
GGAGGTGGAGTTGATGCTAGAGAAAGACATAAACTAGCAGAAAGAGA
AAGAAGAAAATCAATGAGAGAATTATTTCTATCTCTTCACTCGCTAT
TACCTCATTCCAATACGGTGCGTAAAGAACAATCAGCAATTCTCGAT
GAAATTATCAAATATATACCGATTGCTGCTGCTCGTCTTCGTTCACT
TCAGAATCGTAAGGAAAGTAGCAGTAATAATTCATCTAATCATTCTT
CATTGACTTCATCTGCATCTTCATCGAAAGTATCTTCGACCGTGCTT
TCAAAAACAAAATCATATTCTTCAGTACCATCGGTTCAAGTCTCAGA
TCGTGATAACAAGAATAACAATAGTAAAAACTCAGCTACTTCTGCTG
TGGCTAATACGATCATTGACTGTGACATCCGGGTTGCTCCTGAACCT
TCATCTTCTGTGGCGATTCGCATTAGAGGTGACCGGGTGAATGTTTC
TTTAAGTGATTCTAAGGGTACTTCACACACTCTGTTATTATCTGCTG
TTTTAGATGAGCTTGAAAATCATCAACTTGAACTTGTTCGTTCTACT
CATTGTCGCGATGGAAGTAAAGTCTTGCATCATTCCGAAAGCAAGAT
TTGTGATGGACTGGATAAATCTCCCAATTTGTTGAAGTCGAGATTAC
AGGACTTGGCAAGAAAACTTCACAAATTGAGGAAATCGACTTCACTC
AAGAGAACATTCGATCAAATTGAATGATTTGGTTTATTAGTTTTATT
AATTACTTAAATTTTAGTGGTTATAGTAGCGGAGGAAACAGAGTGAT
TGTACAAATGAAATGAGTGGTTGAAGGATCCCAGCTCTGTGTCTTGT
TCGTAATAATAATAAATAAACTAATCTCCACGTTTTCCCTACCAAAC
CTACTCAAATCTCAAAATATACACTCTTCTCTTTCCTTCATGGCACT
TTCTACTATTTCATTATTGCTCATGTGCAAAACGATGATCGTATAAC
AC (SEQ ID NO: 5)

SEQUENCE LISTING

<160> NUMBER OF SEQ ID NOS: 9

<210> SEQ ID NO 1
<211> LENGTH: 885
<212> TYPE: DNA
<213> ORGANISM: Papaver somniferum

<400> SEQUENCE: 1

```
atgatcagta gttattctaa gagtactgac gcagaagtat cgaagaaatc gaggaaaaac     60

acaccagcat catcatcatc atccatggca attgactgga gtagtagtga ttgggaagga    120

aaatcaggat cacaaggagg agtaggagga aatggaggtg gagttgatgc tagagaaaga    180

cataaactag cagaaagaga aagaagaaaa tcaatgagag aattatttct atctcttcac    240

tcgctattac ctcattccaa tacggtgcgt aaagaacaat cagcaattct cgatgaaatt    300

atcaaatata taccgattgc tgctgctcgt cttcgttcac ttcagaatcg taaggaaagt    360

agcagtaata attcatctaa tcattcttca ttgacttcat ctgcatcttc atcgaaagta    420

tcttcgaccg tgctttcaaa aacaaaatca tattcttcag taccatcggt tcaagtctca    480

gatcgtgata acaagaataa caatagtaaa aactcagcta cttctgctgt ggctaatacg    540

atcattgact gtgacatccg ggttgctcct gaaccttcat cttctgtggc gattcgcatt    600

agaggtgacc gggtgaatgt ttctttaagt gattctaagg gtacttcaca cactctgtta    660

ttatctgctg ttttagatga gcttgaaaat catcaacttg aacttgttcg ttctactcat    720

tgtcgcgatg gaagtaaagt cttgcatcat tccgaaagca agatttgtga tggactggat    780

aaatctccca atttgttgaa gtcgagatta caggacttgg caagaaaact tcacaaattg    840

aggaaatcga cttcactcaa gagaacattc gatcaaattg aatga                    885
```

<210> SEQ ID NO 2
<211> LENGTH: 294
<212> TYPE: PRT
<213> ORGANISM: Papaver somniferum

<400> SEQUENCE: 2

```
Met Ile Ser Ser Tyr Ser Lys Ser Thr Asp Ala Glu Val Ser Lys Lys
1               5                   10                  15

Ser Arg Lys Asn Thr Pro Ala Ser Ser Ser Ser Ser Met Ala Ile Asp
            20                  25                  30

Trp Ser Ser Ser Asp Trp Glu Gly Lys Ser Gly Ser Gln Gly Gly Val
        35                  40                  45

Gly Gly Asn Gly Gly Gly Val Asp Ala Arg Glu Arg His Lys Leu Ala
    50                  55                  60

Glu Arg Glu Arg Arg Lys Ser Met Arg Glu Leu Phe Leu Ser Leu His
65                  70                  75                  80

Ser Leu Leu Pro His Ser Asn Thr Val Arg Lys Glu Gln Ser Ala Ile
                85                  90                  95

Leu Asp Glu Ile Ile Lys Tyr Ile Pro Ile Ala Ala Ala Arg Leu Arg
            100                 105                 110

Ser Leu Gln Asn Arg Lys Glu Ser Ser Ser Asn Asn Ser Ser Asn His
        115                 120                 125

Ser Ser Leu Thr Ser Ser Ala Ser Ser Ser Lys Val Ser Ser Thr Val
    130                 135                 140

Leu Ser Lys Thr Lys Ser Tyr Ser Ser Val Pro Ser Val Gln Val Ser
145                 150                 155                 160

Asp Arg Asp Asn Lys Asn Asn Asn Ser Lys Asn Ser Ala Thr Ser Ala
```

```
                165                 170                 175

Val Ala Asn Thr Ile Ile Asp Cys Asp Ile Arg Val Ala Pro Glu Pro
            180                 185                 190

Ser Ser Ser Val Ala Ile Arg Ile Arg Gly Asp Arg Val Asn Val Ser
        195                 200                 205

Leu Ser Asp Ser Lys Gly Thr Ser His Thr Leu Leu Leu Ser Ala Val
    210                 215                 220

Leu Asp Glu Leu Glu Asn His Gln Leu Glu Leu Val Arg Ser Thr His
225                 230                 235                 240

Cys Arg Asp Gly Ser Lys Val Leu His His Ser Glu Ser Lys Ile Cys
                245                 250                 255

Asp Gly Leu Asp Lys Ser Pro Asn Leu Leu Lys Ser Arg Leu Gln Asp
            260                 265                 270

Leu Ala Arg Lys Leu His Lys Leu Arg Lys Ser Thr Ser Leu Lys Arg
        275                 280                 285

Thr Phe Asp Gln Ile Glu
    290


<210> SEQ ID NO 3
<211> LENGTH: 1280
<212> TYPE: DNA
<213> ORGANISM: Papaver somniferum

<400> SEQUENCE: 3

gtagtggagt ggtagttgca gttgattcaa agagattact gtgtcggtcc ataagaccaa     60

tcttctttca tcctccatga tcagtagtta ttctaagagt actgacgcag aagtatcgaa    120

gaaatcgagg aaaaacacac cagcatcatc atcatcatcc atggcaattg actggagtag    180

tagtgattgg gaaggaaaat caggatcaca aggaggagta ggaggaaatg gaggtggagt    240

tgatgctaga gaaagacata aactagcaga aagagaaaga agaaaatcaa tgagagaatt    300

atttctatct cttcactcgc tattacctca ttccaatacg gtgcgtaaag aacaatcagc    360

aattctcgat gaaattatca aatatatacc gattgctgct gctcgtcttc gttcacttca    420

gaatcgtaag gaaagtagca gtaataattc atctaatcat tcttcattga cttcatctgc    480

atcttcatcg aaagtatctt cgaccgtgct ttcaaaaaca aaatcatatt cttcagtacc    540

atcggttcaa gtctcagatc gtgataacaa gaataacaat agtaaaaact cagctacttc    600

tgctgtggct aatacgatca ttgactgtga catccgggtt gctcctgaac cttcatcttc    660

tgtggcgatt cgcattagag gtgaccgggt gaatgtttct ttaagtgatt ctaagggtac    720

ttcacacact ctgttattat ctgctgtttt agatgagctt gaaaatcatc aacttgaact    780

tgttcgttct actcattgtc gcgatggaag taaagtcttg catcattccg aaagcaagat    840

ttgtgatgga ctggataaat ctcccaattt gttgaagtcg agattacagg acttggcaag    900

aaaacttcac aaattgagga aatcgacttc actcaagaga acattcgatc aaattgaatg    960

atttggttta ttagttttat taattactta aattttagtg gttatagtag cggaggaaac   1020

agagtgattg tacaaatgaa atgagtggtt gaaggatccc agctctgtgt cttgttcgta   1080

ataataataa ataaactaat ctccacgttt tccctaccaa acctactcaa atctcaaaat   1140

atacactctt ctctttcctt catggcactt tctactattt cattattgct catgtgcaaa   1200

acgatgatcg tataacacca aagcgatctt ctctttcctt tacactacag tagttgcttt   1260

ctgtatccaa aatctgccac                                                1280
```

<210> SEQ ID NO 4
<211> LENGTH: 2116
<212> TYPE: DNA
<213> ORGANISM: Papaver somniferum

<400> SEQUENCE: 4

```
gtagtggagt ggtagttgca gttgattcaa agagattact gtgtcggtcc ataagaccaa     60
tcttctttca tcctccatga tcagtagtta ttctaagagt actgacgcag aagtatcgaa    120
gaaatcgagg aaaaacacac cagcatcatc atcatcatcc atggcaattg actggagtag    180
tagtgattgg gaaggaaaat caggatcaca aggaggagta ggaggaaatg gaggtggagt    240
tgatgctaga gaaagacata aactagcaga aagagaaaga agaaaatcaa tgagagaatt    300
atttctatct cttcactcgc tattacctca ttccaatacg gtgcgtaaag aacaatcagc    360
aattctcgat gaaattatca aatatatacc gattgctgct gctcgtcttc gttcacttca    420
gaatcgtaag gaaagtagca gtaataattc atctaatcat tcttcattga cttcatctgc    480
atcttcatcg aaagtatctt cgaccgtgct ttcaaaaaca aaatcatatt cttcagtacc    540
atcggttcaa gtctcagatc gtgataacaa gaataacaat agtaaaaact cagctacttc    600
tgctgtggct aatacgatca ttgactgtga catccgggtt gctcctgaac cttcatcttc    660
tgtggcgatt cgcattagag gtgaccgggt gaatgtttct ttaagtgatt ctaagggtac    720
ttcacacact ctgttattat ctgctgtttt agatgagctt gaaaatcatc aacttgaact    780
tgttcgttct actcattgtc gcgatggaag taaagtcttg catcattccg aaagcaaggt    840
ttgtttctta atttcttttt tctttaatga tccgtgattc gcttttgttt tttgaatgat    900
ttgtttttta attattactt tatcaatgat atcagctctg attctgagta tcttctagta    960
tatgtatatt gtgtacttgc tgaatcggga atgtgattat tctattgcta gagatctgtg   1020
ttctgctgta gactcacgat ctagctttca gaatcatgtg tcaaatcttt gaatttcagt   1080
tcacataaaa ttttagttgg gatagttttc ttcgcttttg aagatcccga ttctctttta   1140
tctgacacat tattcatttt gttaatgcgt tttaggtatc attattagtt ttaattatta   1200
ttatctaact agacatgttt tttcttttgg cagatttgtg atggactgga taaatctccc   1260
aatttgttga agtcgagatt acaggacttg gcaagaaaac ttcacaaatt gaggaaatcg   1320
acttcactca agagaacatt cgatcaaatt gaatgatttg gtttattagt tttattaatt   1380
acttaaattt tagtggttat agtagcggag gaaacagagt gattgtacaa atgaaatgag   1440
tggttgaagg atcccagctc tgtgtcttgt tcgtaataat aataaataaa ctaatctcca   1500
cgttttccct accaaaccta ctcaaatctc aaaatataca ctcttctctt tccttcatgg   1560
cactttctac tatttcatta ttgctcatgt gcaaaacgat gatcgtataa caccaaagcg   1620
atcttctctt tcctttacac tacagtagtt gctttctgta tccaaaatct gccaccaaca   1680
tttgtccccg aaatgcgtta attacccgtt catcacacat agtttcgtgt gggatgctct   1740
aaaaaagaat cgtcactttt agatctgtga tttagacgga tacagtaaat tatgtggtta   1800
ctgtggttat aatagtgttg ctttgtgtag atttggtaca ccttcgtata atttggtcat   1860
ttggtgttca tgtaacaatc tttcagaaac atctattcat gattcactca ttcatacaaa   1920
gaaattagta gccttgatct tcaacaggcc agtggatgag ttttagaaac tttaaagaaa   1980
acaaggatat actacaaaga aagattattt tatttcttaa ataattttag aaagaagaaa   2040
tcatggggtg gacgtcttaa tcaagagaaa gttgaggtga ctccactaag tgagatgaaa   2100
gttggatgta aacgtg                                                   2116
```

<210> SEQ ID NO 5
<211> LENGTH: 1224
<212> TYPE: DNA
<213> ORGANISM: Papaver somniferum

<400> SEQUENCE: 5

```
gaaggtgtag tggagtggta gttgcagttg attcaaagag attactgtgt cggtccataa     60

gaccaatctt ctttcatcct ccatgatcag tagttattct aagagtactg acgcagaagt    120

atcgaagaaa tcgaggaaaa acacaccagc atcatcatca tcatccatgg caattgactg    180

gagtagtagt gattgggaag gaaaatcagg atcacaagga ggagtaggag gaaatggagg    240

tggagttgat gctagagaaa gacataaact agcagaaaga gaaagaagaa aatcaatgag    300

agaattattt ctatctcttc actcgctatt acctcattcc aatacggtgc gtaaagaaca    360

atcagcaatt ctcgatgaaa ttatcaaata tataccgatt gctgctgctc gtcttcgttc    420

acttcagaat cgtaaggaaa gtagcagtaa taattcatct aatcattctt cattgacttc    480

atctgcatct tcatcgaaag tatcttcgac cgtgctttca aaaacaaaat catattcttc    540

agtaccatcg gttcaagtct cagatcgtga taacaagaat aacaatagta aaaactcagc    600

tacttctgct gtggctaata cgatcattga ctgtgacatc cgggttgctc ctgaaccttc    660

atcttctgtg gcgattcgca ttagaggtga ccgggtgaat gtttctttaa gtgattctaa    720

gggtacttca cacactctgt tattatctgc tgttttagat gagcttgaaa atcatcaact    780

tgaacttgtt cgttctactc attgtcgcga tggaagtaaa gtcttgcatc attccgaaag    840

caagatttgt gatggactgg ataaatctcc caatttgttg aagtcgagat tacaggactt    900

ggcaagaaaa cttcacaaat tgaggaaatc gacttcactc aagagaacat tcgatcaaat    960

tgaatgattt ggtttattag ttttattaat tacttaaatt ttagtggtta tagtagcgga   1020

ggaaacagag tgattgtaca aatgaaatga gtggttgaag gatcccagct ctgtgtcttg   1080

ttcgtaataa taataaataa actaatctcc acgttttccc taccaaacct actcaaatct   1140

caaaatatac actcttctct ttccttcatg gcactttcta ctatttcatt attgctcatg   1200

tgcaaaacga tgatcgtata acac                                          1224
```

<210> SEQ ID NO 6
<211> LENGTH: 24
<212> TYPE: DNA
<213> ORGANISM: artificial sequence
<220> FEATURE:
<223> OTHER INFORMATION: primer

<400> SEQUENCE: 6

```
gaaggggtag tggagtggta gttg                                            24
```

<210> SEQ ID NO 7
<211> LENGTH: 23
<212> TYPE: DNA
<213> ORGANISM: artificial sequence
<220> FEATURE:
<223> OTHER INFORMATION: primer

<400> SEQUENCE: 7

```
gtgttatacg atcatcgttt tgc                                             23
```

<210> SEQ ID NO 8
<211> LENGTH: 42
<212> TYPE: DNA
<213> ORGANISM: artificial sequence -continued

```
<220> FEATURE:
<223> OTHER INFORMATION: primer 470

<400> SEQUENCE: 8

agttgttgat tcagaattgt cattcaattt gatcgaatgt tc                        42


<210> SEQ ID NO 9
<211> LENGTH: 42
<212> TYPE: DNA
<213> ORGANISM: artificial sequence
<220> FEATURE:
<223> OTHER INFORMATION: primer 471

<400> SEQUENCE: 9

agttgttgat tcagaattga tgatcagtag ttattctaag ag                        42
```

PAPAVER SOMNIFERUM PLANTS WITH A MODIFIED TRANSCRIPTION FACTOR GENE IN THE REGULATION OF BENZYLISOQUINOLINE ALKALOIDS SYNTHESIS

CROSS REFERENCE TO RELATED APPLICATIONS

This is the U.S. National Stage of International Application No. PCT/IB2022/054862, filed May 24, 2022, which was published in English under PCT Article 21(2), which in turn claims the benefit of Great Britain Application No. 2107438.0, filed May 25, 2021, which is incorporated herein in its entirety.

FIELD OF THE INVENTION

The disclosure relates to transcription cassettes and vectors comprising a nucleotide sequence encoding a transcription factor and wherein the transcription factor controls expression of genes that encode polypeptides involved in the production of plant benzylisoquinoline (BIA) alkaloids such as for example, morphine, codeine, oripavine and thebaine, the disclosure further relates to plants, plant cells/cultures and seeds that are genetically engineered to include a recombinant copy or copies of the nucleic acid encoding said transcription factor to increase expression of said transcription factor thereby modifying BIA manufacture processes for the cultivation of the genetically engineered plants or plant cell cultures and for the modulation of BIAs and processes for the extraction of BIAs from the genetically engineered plants or plant cell cultures.

The Sequence Listing is submitted as an ASCII text file in the form of the file named 8617-111122-01_Sequence_Listing.txt, which was created on Nov. 19, 2023, and is 11,230 bytes, which is incorporated by reference herein.

BACKGROUND TO THE INVENTION

The opium poppy, *Papaver somniferum* is an important source of a variety of BIAs. Due to their narcotic and analgesic properties, some BIAs, and their derivatives, are desired for use in therapy. *P. somniferum* is a source of clinically useful alkaloids such as morphine, codeine, thebaine, noscapine and papaverine. BIAs are extracted from latex harvested from the green seed pods of opium poppy or from the poppy straw which is the dried mature plant. The pathway to produce alkaloids and the various genes involved in the pathway are known and are disclosed in U.S. application Ser. Nos. 15/182,761 and 15/304,455 the contents of which are hereby incorporated by reference in their entirety. Morphinan alkaloids such as codeine and morphine are known to derive from the intermediate (R)-reticuline. (R)-reticuline is thought to be formed by its enantiomer (S)-reticuline in a two-step isomerization process. (R)-reticuline is then further transformed to thebaine. Thebaine is transformed either to oripavine to morphinone and morphine or via an alternative route to codeinone and codeine which is then subsequently transformed to morphine.

Various attempts to increase the content of alkaloids in planta have been attempted by natural breeding methods or reverse genetics shifting the alkaloid pathway to increase intermediate and end-products such as for example obtaining plants with increased thebaine or codeine content; see WO2016/207643; WO2017/112011; EP3398430. Plants comprising knock out mutations are disclosed in patent application No U.S. Ser. No. 14/375,120 the content of which is hereby incorporated by reference. Alternative methods to modulate plant metabolism are described in WO2021/026119 by overexpressing a transcription factor that positively regulates nicotine biosynthesis. Modified *Nicotiana tabacum* plants comprised increased nicotine levels in tobacco leaves.

Fast Neutron Mutagenesis (FNM) was carried out on seed of a morphine & noscapine producing *P. sominferum* cultivar. The mutagenized M1 seed was sown and the M1 generation self-pollinated to generate M2 seed. The M2 generation was then screened for any unusual metabolite profiles compared to the non-mutagenized parental variety. The screen identified two independent mutants that no longer accumulate any BIAs and no longer express most BIA biosynthesis genes. Molecular characterisation of the mutants at the DNA level revealed that each mutant carries a unique deletion spanning a shared region encoding a transcription factor. Because of the loss of BIA synthesis gene expression and lack of BIA accumulation in the mutants, the transcription factor was named REGULATOR OF BENZYLISOQUINOLINE ALKALOIDS (RBA) and the mutants retrospectively labelled rba-1 and rba-2 mutants.

This disclosure characterises a transcription factor that controls the expression of genes involved in the production of BIAs such as morphinan alkaloids.

STATEMENTS OF INVENTION

According to an aspect of the invention there is provided an expression cassette adapted for plant expression comprising a nucleic acid molecule selected from:

i) a nucleic acid molecule comprising a nucleotide sequence as set forth in SEQ ID NO: 1;
ii) a nucleic acid molecule the complementary strand of which hybridizes under stringent hybridization conditions to the sequence in SEQ ID NO: 1 wherein said nucleic acid molecule encodes a transcription factor;
iii a nucleic acid molecule comprising a nucleotide sequence that encodes a polypeptide comprising an amino acid sequence as set forth in SEQ ID NO: 2;
iv) nucleic acid molecule comprising a nucleotide sequence that encodes a polypeptide comprising an amino acid sequence wherein said amino acid sequence is modified by addition, deletion or substitution of at least one amino acid residue as represented in ii) above and wherein said polypeptide is a transcription factor and said transcription factor controls transcription of said one or more genes involved in the synthesis of benzylisoquinoline alkaloids.

Hybridization of a nucleic acid molecule occurs when two complementary nucleic acid molecules undergo an amount of hydrogen bonding to each other. Isolated nucleic acid molecules as referred herein include genomic DNA, cDNA molecules and RNA molecules. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N Y, 2001); and Tijssen, Laboratory Techniques in Biochemistry and Molecular Biology-Hybridization with Nucleic Acid Probes Part I, Chapter 2 (Elsevier, New York, 1993). The Tm is the temperature at which 50% of a given strand of a nucleic acid molecule is hybridized to its complementary strand. The following is an exemplary set of hybridization conditions and is not limiting:

Very High Stringency (allows sequences that share at least 90% identity to hybridize)

Hybridization: 5×SSC at 65° C. for 16 hours

Wash twice: 2×SSC at room temperature (RT) for 15 minutes each

Wash twice: 0.5×SSC at 65° ° C. for 20 minutes each

High Stringency (allows sequences that share at least 80% identity to hybridize)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (allows sequences that share at least 50% identity to hybridize)

Hybridization: 6×SSC at RT to 55° C. for 16-20 hours

Wash at least twice: 2×-3×SSC at RT to 55° C. for 20-30 minutes each.

In a preferred embodiment of the invention said transcription factor is a helix loop helix transcription factor.

In a preferred embodiment of the invention said isolated nucleic acid molecule is at least 50% identical to the nucleotide sequence set forth in SEQ ID NO: 1.

Preferably, the isolated nucleic acid molecule is at least 55%, 60%, 65%, 70%, 75%, 80%, 90%, 91%, 92%, 93%, 94%, 95%, 96%, 97%, 98% or 99% identical to the nucleotide sequence set forth in SEQ ID NO: 1 over the full-length nucleotide sequence.

In a preferred embodiment of the invention said nucleic acid molecule comprises or consists of sequence ID NO 1, or polymorphic sequence variant thereof.

In a preferred embodiment said nucleic acid encodes a polypeptide comprising or consisting of an amino acid sequence set forth in SEQ ID NO 2, or polymorphic sequence variant thereof.

A modified polypeptide as herein disclosed may differ in amino acid sequence by one or more substitutions, additions, deletions, truncations that may be present in any combination and includes polymorphic sequence variants that the skilled person would expect to exist in nature. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the same biological function and activity as the reference polypeptide from which it varies.

In a preferred embodiment of the invention said modified polypeptide is a variant and is at least 50%, 55%, 59%, 60%, 65%, 70%, 75%, 80%, 85%, 90%, 95%, 96%, 97%, 98% or 99% similar to the amino acid sequence set forth in SEQ ID NO: 2 over the full amino acid sequence.

In a preferred embodiment of the invention said modified polypeptide is a variant and is at least 50%, 55%, 59%, 60%, 65%, 70%, 75%, 80%, 85%, 90%, 95%, 96%, 97%, 98% or 99% identical to the amino acid sequence set forth in SEQ ID NO: 2 over the full amino acid sequence.

In a preferred embodiment said one or more genes involved in the synthesis of benzylisoquinoline alkaloids are selected from: thebaine synthase, salutaridine reductase, salutaridinol 7-O-acetyltransferase, salutaridine synthase, codeine O-demethylase, codeinone reductase, thebaine 6-O-demethylase, (S)-to-(R)-reticuline P450-oxidoreductase, O-methyltransferase 1, canadine synthase, O-methyltransferase 3, cytochrome P450 CYP82Y1, O-methyltransferase 2, acetyltransferase 1, cytochrome P450 CYP82X2, cytochrome P450 CYP82X1, carboxylesterase 1, short-chain dehydrogenase/reductase, (S)-tetrahydroprotoberberine-cis-N-methyltransferase berberine bridge enzyme, 3'-hydroxy-N-methylcoclaurine 4'-O-methyltransferase 2, 3'-hydroxy-N-methylcoclaurine 4'-O-methyltransferase 1, (S)—N-methylcoclaurine 3'-hydroxylase, coclaurine N-methyltransferase, norcoclaurine 6-O-methyltransferase, S-norcoclaurine synthase 1, protopine 6-hydroxylase, norreticuline-7-O-methyltransferase, 3'-hydroxy-N-methylcoclaurine 4'-O-methyltransferase 2,3'-hydroxy-N-methylcoclaurine 4'-O-methyltransferase 1, (S)—N-methylcoclaurine 3'-hydroxylase, coclaurine N-methyltransferase, norcoclaurine 6-O-methyltransferase, S-norcoclaurine synthase 1, (S)-tetrahydroprotoberberine-cis-N-methyltransferase, norreticuline-7-O-methyltransferase, scoulerine O-demethylase.

In a preferred embodiment said one or more genes involved in the synthesis of benzylisoquinoline alkaloids are selected from the genes listed in Table 2.

In a preferred embodiment of the invention said nucleic acid molecule is operably linked to a transcription promoter.

In an alternative preferred embodiment of the invention said transcription promoter is a heterologous promoter.

In an alternative preferred embodiment said transcription promoter is an endogenous promoter that naturally controls transcription of said transcription factor.

In a preferred embodiment of the invention said transcription promoter is an inducible promoter.

In an alternative preferred embodiment of the invention said transcription promotor is a constitutive promoter.

In an alternative preferred embodiment of the invention said promoter is a tissue specific promoter.

In a further preferred method of the invention said promotor is selected from the group consisting of CaMV 35S promoter and *Glycine Max* Ubiquitin 3 promoter.

By "transcription promoter" is meant a nucleotide sequence upstream from the transcriptional initiation site and which contains all the regulatory regions required for transcription. Said promoters include viral, fungal, bacterial, animal and plant-derived promoters capable of functioning in plant cells. Constitutive promoters include, for example CaMV 35S promoter (Odell et al. (1985) Nature 313, 9810-812); rice actin (McElroy et al. (1990) Plant Cell 2: 163-171); ubiquitin (Christian et al. (1989) Plant Mol. Biol. 18 (675-689); pEMU (Last et al. (1991) Theor Appl. Genet. 81: 581-588); MAS (Velten et al. (1984) EMBO J. 3. 2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680, 5,268,463; and 5,608,142, each of which is incorporated by reference.

Chemical-regulated promoters can be used to modulate the expression of a gene in a plant through the application of an exogenous chemical regulator. Depending upon the objective, the promoter may be a chemical-inducible promoter, where application of the chemical induced gene expression, or a chemical-repressible promoter, where application of the chemical represses gene expression. Chemical-inducible promoters are known in the art and include, but are not limited to, the maize In2-2 promoter, which is activated by benzene sulphonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88: 10421-10425 and McNellis et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference.

Where enhanced expression in particular tissues is desired, tissue-specific promoters can be utilised. Tissue-specific promoters include those described by Yamamoto et al. (1997) Plant J. 12(2): 255-265; Kawamata et al. (1997) Plant Cell Physiol. 38(7): 792-803; Hansen et al. (1997) Mol. Gen. Genet. 254(3): 337-343; Russell et al. (1997) Transgenic Res. 6(2): 157-168; Rinehart et al. (1996) Plant Physiol. 112(3): 1331-1341; Van Camp et al. (1996) Plant Physiol. 112(2): 525-535; Canevascni et al. (1996) Plant Physiol. 112(2): 513-524; Yamamoto et al. (1994) Plant Cell Physiol. 35(5): 773-778; Lam (1994) Results Probl. Cell Differ. 20: 181-196; Orozco et al. (1993) Plant Mol. Biol. 23(6): 1129-1138; Mutsuoka et al. (1993) Proc. Natl. Acad. Sci. USA 90 (20): 9586-9590; and Guevara-Garcia et al (1993) Plant J. 4(3): 495-50.

"Operably linked" means functionally associated as part of the same nucleic acid molecule, suitably positioned and oriented for transcription to be initiated from the promoter. DNA operably linked to a promoter is "under transcriptional initiation regulation" of the promoter.

According to an aspect of the invention there is provided a vector comprising an expression cassette according to the invention.

In a preferred embodiment of the invention said expression vector is a transposon.

In an alternative embodiment of the invention said vector is a viral based vector.

Of interest in the present context are nucleic acid constructs which operate as plant vectors. Specific procedures and vectors previously used with wide success in plants are described by Guerineau and Mullineaux (1993) (Plant transformation and expression vectors. In: Plant Molecular Biology Labfax (Croy RRD ed) Oxford, BIOS Scientific Publishers, pp 121-148. Suitable vectors may include plant viral-derived vectors (see e.g. EP194809). If desired, selectable genetic markers may be included in the construct, such as those that confer selectable phenotypes such as resistance to herbicides (e.g. kanamycin, hygromycin, phosphinotricin, chlorsulfuron, methotrexate, gentamycin, spectinomycin, imidazolinones and glyphosate).

According to a further aspect of the invention there is provided a plant wherein said plant is transformed or transfected with a transcription cassette or expression vector according to the invention.

Preferably, said plant is of the genus *Papaver* spp.

Genes involved in the pathway of producing benzylisoquinoline alkaloids are known in the art and encode polypeptides with cytochrome p450 and methyltransferase activity. Deletion of one or more genes in this pathway can alter the levels of one or more benzylisoquinoline alkaloids such as the deletion of codeine 3-O-demethylase results in *Papaver somniferum* plants with increased content of codeine, whereas deletion of thebaine 6-O-demethylase results in increased content of thebaine and oripavine. Plants with altered benzylisoquinoline alkaloids pathways are known in the art and disclosed in, for example, PCT/GB2017/050068 and EP3398430.

In a preferred embodiment of the invention said plant is selected from: *Papaver somniferum, P. setigerum, P. bracteatum, P. orientale, P. pseudo-orientale, P. lasiothrix, P. cylindricum, P. fugax, P. triniifolium.*

In a preferred embodiment of the invention said plant is a *Papaver somniferum* plant.

Benzylisoquinoline alkaloids include oripavine, codeine, thebaine, morphine, noscapine, morphinone, codeinone, reticuline, scoulerine, papaverine, cryptopine, laudanosine, protopine, O-methylsomniferin.

In a preferred embodiment of the invention expression of said transcription factor from said transcription cassette or expression vector encoding is increased when compared to a non-transformed plant of the same species.

In the context of this invention the expression "increased expression levels" relates to increased transcription subsequently resulting in higher nucleic acid transcript levels in said transformed plant when compared to an untransformed plant. Said increased transcript levels can be measured by, for example, quantitative PCR. Increased expression can be achieved by increasing the rate of transcription and/or by increasing the copy number of genes encoding the basic helix-loop-helix transcription factor according to the invention.

In a preferred embodiment of the invention said expression levels are increased by at least 2, 3, 4, 5, or 10-fold.

In a preferred embodiment of the invention said transformed plant or plant material thereof comprises at least two copies of said nucleic acid molecule.

In a further preferred embodiment of the invention said transformed plant or plant material thereof comprises 3 or more copies of said nucleic acid molecule encoding the basic helix-loop-helix transcription factor according to the invention.

In a preferred embodiment of the invention said transformed plant or plant cell comprises increased content of one or more BIAs when compared to an untransformed *Papaver* plant or plant cell.

The total sum of benzylisoquinoline alkaloids weight is the sum of the weight of oripavine, codeine, thebaine, morphine, noscapine, morphinone, codeinone, reticuline, scoulerine, papaverine, cryptopine, laudanosine, protopine and O-methylsomniferine, or more preferably, the sum of the weight of codeine, morphine, thebaine, noscapine and oripavine, or even more preferably, the sum of the weight of codeine, morphine, thebaine and oripavine.

In a preferred embodiment of the invention said levels are increased by 2, 3, 4, 5 or 10-fold.

According to a further aspect of the invention there is provided plant material obtained from the plant according to the invention.

Plant material in the context of this invention refers to leaves, capsules or seeds.

According to a further aspect of the invention there is provide a plant cell transformed or transfected with a transcription cassette or an expression vector according to the invention.

According to a further aspect of the invention there is provide a plant cell culture comprising a transformed plant cell according to the invention.

In a preferred embodiment of the invention said plant cell is a *Papaver* spp plant cell.

In a preferred embodiment of the invention said plant cell is selected from the group consisting of *Papaver somniferum, P. setigerum, P. bracteatum, P. orientale, P. pseudo-orientale, P. lasiothrix, P. cylindricum, P. fugax, P. triniifolium.*

In a preferred embodiment of the invention said plant cell is a *Papaver somniferum* cell.

According to a further aspect of the invention there is provided a bioreactor comprising a plant cell culture according to the invention.

According to a further aspect of the invention there is provided a method to produce one or more benzylisoquinoline alkaloids comprising:

i) forming a cell culture comprising a transformed or transfected cell according to the invention in cell culture vessel;
ii) culturing said cell culture in the presence of one or more benzylisoquinoline alkaloids or benzylisoquinoline precursors; and optionally
iii) extracting one or more benzylisoquinoline alkaloids from the cells or cell culture.

According to an aspect of the invention there is provided a process for the extraction of from a *Papaver* plant comprising the steps:

i) harvesting a plant or plant material prepared from a plant according to the invention;
ii) forming a reaction mixture of particulate plant material;
iii) extraction of the reaction mixture to provide an alkaloid enriched fraction;
and optionally
iv) concentrating said alkaloid enriched fraction to provide an alkaloid enriched fraction.

In a preferred method of the invention said plant material comprises poppy capsule, poppy straw and/or poppy latex.

According to a further aspect of the invention there is provided a method to produce a plant that has altered expression of a polypeptide according to the invention comprising the steps of:

i) transforming a *Papaver* plant with a vector according to the invention, obtaining seed from the plant under i)
iii) cultivating said seed in ii) to produce first and subsequent generations of plants;
iv) obtaining seed from the first-generation plant and subsequent generations of plants.

In a preferred embodiment of the invention said plant is of the genus *Papaver* spp.

In a preferred method of the invention said *Papaver* plant is selected from: *Papaver somniferum, P. setigerum, P. bracteatum, P. orientale, P. pseudo-orientale, P. lasiothrix, P. cylindricum, P. fugax, P. triniifolium.*

According to a further aspect of the invention there is provided a plant obtained by the method according to the invention.

According to a further aspect of the invention there is provided a *Papaver* plant, or plant part thereof, comprising a gene encoding a transcription factor comprising a nucleotide sequence set forth in SEQ ID NO: 1, or a polymorphic sequence variant of SEQ ID NO: 1 wherein said nucleotide sequence is modified wherein the modified nucleotide sequence encodes a transcription factor with reduced or undetectable transcription factor activity.

In a preferred embodiment of the invention said nucleotide sequence is modified by addition, deletion or substitution of at least one nucleotide base.

In a preferred embodiment of the invention said *Papaver* plant is modified wherein said modification is the deletion of all or part of the nucleotide sequence set forth in SEQ ID NO: 1, or a polymorphic sequence variant of SEQ ID NO:1.

In a preferred embodiment of the invention said plant part thereof is a *Papaver* capsule.

In an alternative preferred embodiment said plant part thereof is a *Papaver* seed.

In a preferred embodiment of the invention said *Papaver* plant, capsule or seed substantially lacks benzylisoquinoline alkaloids or benzylisoquinoline precursors.

In a preferred embodiment of the invention said *Papaver* plant, or plant part thereof, is selected from: *Papaver somniferum, P. setigerum, P. bracteatum, P. orientale, P. pseudo-orientale, P. lasiothrix, P. cylindricum, P. fugax, P. triniifolium.*

In a preferred embodiment of the invention said *Papaver* plant is *Papaver somniferum.*

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. Where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures and tables:

FIG. 1: Schematic representation of the deletions in the rba-1 and rba-2 mutants; and FIG. 2: Nucleotide and amino acid sequences of RBA.

FIG. 3: Map of pRI 201-AN_35 S:RBA

MATERIALS AND METHODS

Growth of Plant Material

All plant material was grown under glass in 16 hour days at the University of York horticulture facilities. The growth substrate consisted of 4 parts John Innes No. 2, 1 part Perlite and 2 parts Vermiculite.

Crosses and Self-Pollinations

Mother plants used for crosses were emasculated at the hook stage of flower development. At the time of anthesis emasculated flowers were fertilised with pollen from synchronously developing father plants. To prevent contaminating pollen from reaching the receptive stigmas, emasculated flowers were covered with micro perforated clear bakery bags until four days after fertilisation.

Self-pollination was ensured by covering the flowers shortly before onset of anthesis with micro perforated clear bakery bags and manually pollinating the flower at anthesis.

Fast Neutron Deletion Mutagenesis and Glasshouse-Based Forward Screening

Fast neutron mutagenesis (FNM) was carried out by the HAS Centre for Energy Research, Radiation Protection Department, H-1121 Budapest, Konkoly Thege út 29-33, X. epulet, Hungary. About 40 g of seed of the Sun Pharmaceutical Industries (Australia) cultivar High Noscapine 4 (HN4) were exposed to 20 Gy (beam time 50 min). The M1 generation was self-pollinated. One M2 plant per M2 seed family was screened. Latex was collected from 9 weeks old M2 seedlings and analysed. M2 plants displaying an altered alkaloid composition in the latex compared to HN4 controls were grown to maturity to confirm the phenotype in dry M2 capsule material. M3 seed was collected from M2 plants with confirmed phenotypes. Five M3 plants were then grown per M2 mutant plant to confirm the heritability of the phenotype in mature dry M3 capsule material. The rba-1 and rba-2 mutants were further propagated through self-pollinations to the M5 generation with each of the successive generations being phenotyped to confirm the 'loss of all BIAs" phenotype. All generations were grown in the glasshouse.

Leaf Latex and Dry Capsule Analysis of Glasshouse Grown Material

Latex was collected from 9 weeks old plants from cut petioles, with a single drop dispersed into 500 μL of 10% acetic acid. This was diluted 10 fold in 1% acetic acid to give an alkaloid solution in 2% acetic acid for further analysis. Capsules were harvested from the same plants used for latex analysis and single capsules were ground to a fine powder in a ball mill (Model MM04, Retsch, Haan, Germany). Samples of ground poppy straw were then weighed accurately to 10±0.1 mg and extracted in 0.5 ml of a 10% acetic acid solution with gentle shaking for 1 h at room temperature. Samples were then clarified by centrifugation and a 50 μl subsample diluted 10 fold in 1% acetic acid to give an alkaloid solution in 2% acetic acid for further analysis.

All solutions were analysed using a Waters Acquity UPLC system (Waters Ltd., Elstree, UK) fitted with a Waters Acquity BEH C18 column, 2.1 mm×100 mm with 1.7 micron packing. The mobile phase used a gradient profile with eluent A consisting of 10 mM ammonium bicarbonate of pH 10.2 and eluent B methanol. The mobile phase gradient conditions used are shown in the table below with a linear gradient. The flow rate was 0.5 ml per minute. The column temperature was maintained at 60° C. The injection volume was 2 μl. The eluted peaks were ionised in positive APCI mode and detected within 5 ppm mass accuracy using a Thermo LTQ-Orbitrap. The runs were controlled by Thermo Xcalibur software (Thermo Fisher Scientific Inc., Hemel Hempstead, UK).

| TIME [min] | % Eluent A | % Eluent B | Flow [mL/min] |
|---|---|---|---|
| 0.0 | 98 | 2 | 0.50 |
| 0.2 | 98 | 2 | 0.50 |
| 0.5 | 60 | 40 | 0.50 |
| 4.0 | 20 | 80 | 0.50 |
| 4.5 | 20 | 80 | 0.50 |

All data analysis was carried out using the R programming language and custom scripts. Standards for morphine, oripavine, codeine, thebaine and noscapine were used to identify and quantify these alkaloids using exact mass, retention time and peak areas for the pseudomolecular ion. Other putative alkaloid peaks were quantified by their pseudomolecular ion areas relative to the thebaine standard. For putative alkaloids, the Bioconductor rcdk package (Guha, (2007) J. Stat. Software 6(18)) was used to generate pseudomolecular formulae from exact masses within elemental constraints C=1-100, H=1-200, O=0-200, N=0-3 and mass accuracy <5 ppm. The hit with the lowest ppm error within these constraints was used to assign a putative formula.

Plant Material for Genome Sequencing

Three weeks old rba-1 (M5 generation) and rba-2 (seM4 generation) mutant seedlings were used for DNA extraction. The seedling material was grown in complete darkness for 24 hours prior to harvest. Seedlings were severed from their primary root, flash frozen in liquid nitrogen and stored at −80° C. until shipment on dry ice to Amplicon Express, Inc. (Pullman, WA, USA) for DNA extraction.

Genome Sequencing

High quality genomic DNA was prepared from the seedling material by Amplicon Express using their inhouse NGS-Grade genomic DNA preparation protocol optimised for long reads on various NextGenerationSequencing (NGS) platforms such as Chromium. The DNA preparations were shipped directly to HudsonAlphas (HudsonAlpha Institute for Biotechnology, 601 Genome Way, Huntsville, AL 35806) where Chromium libraries were constructed for each sample for the 10× Genomics Platform and sequenced with Illumina NovaSeq technology after quality control of the DNA samples. In total, 180 billion bases (2×91,141,870,748 and 2×91,161,893,801 respectively) were generated for each of the rba-1 and rba-2 mutant samples (named TC06 and TC07, respectively) in the resulting datasets that consist of 2×600 million (2×603,588,548 and 2×603,721,151 respectively) pair-ended 150 bases long sequence reads. Based on the 2.7 Gb size of the HN1 reference genome (ASM357369v1), this represents approximately 60 times sequencing depth for each base position for the two mutants.

Genome Assembly

The draft genomes TC06 and TC07, respectively, for the rba-1 and rba-2 mutants were assembled with the Supernova (version2.1.1), a 10× Genomics Linked-Read Diploid De Novo Assembler (support.10xgenomics.com/de-novo-assembly/software/overview/latest/performance) on the Viking high performance computing cluster at the University of York. The TC06 (rba-1) mutant assembly has a total size of 2.6 Gb (2,581,235,059) with 67,648 scaffolds and a scaffold N50 of 836 kb (836,342), and the TC07 (rba-2) mutant assembly has a total size of 2.5 Gb (2,459,139,609) with 87,225 scaffolds and a scaffold N50 of 210 kb (209,519).

Identification of Candidate Scaffolds Containing the Overlapping Deletion Regions in Genome Assemblies of the Rba-1 and Rba-2 Mutants The whole 51,213 annotated protein coding gene transcripts of the HN1 reference genome were used to perform BLASTN searches against both TC06 (rba-1) and TC07 (rba-2) mutant assemblies. The top scaffold hits were ordered for each gene based on the positions of each gene in the reference genome. It is expected that each scaffold would appear as top matches for a stretch of consecutive reference genes as the mutant genome is near identical to the reference genome. When a scaffold matches two such stretches but is interrupted by one or more genes in between with low matching top hits scores it was identified as a potential candidate for carrying a deleted region in the mutant genome. Two such scaffolds, TC06_scaffold_251445 in the TC06 (rba-1) assembly and TC07_scaffold_186274 in the TC07 (rba-2) assembly, were identified as potentially carrying overlapping deletions corresponding to the same region on chromosome 9 in the reference genome.

In Silico Characterisation of Deletions in Candidate Scaffolds

Firstly, dotplot analysis was used to confirm and locate the putative deletions for the above two scaffolds. A dotplot analysis is a graphic representation of the comparison of two sequences which identifies regions of close similarity after sequence alignment. A dot plot is a two-dimensional similarity matrix that have the two sequences being compared along the vertical and horizontal axes. For a simple visual representation of the similarity between two sequences, individual dots in the matrix are painted black if a defined length of bases are identical, so that matching sequence segments appear as runs of diagonal lines across the matrix. As a result, when two DNA sequences are completely identical, a solid diagonal line with a downward slope will appear. If two DNA sequences are in reverse complement to each other, a solid diagonal line with an upward slope will appear. When two sequences are random, no continuous line pattern would appear. Thus, a dotplot result would identify potential deletions as well as inversions between two sequences. Corresponding regions to both scaffolds (TC06_scaffold_251445 and TC07_scaffold_186274) were retrieved from the HN1 reference genome and compared to the respective scaffolds with Gepard dotplot tool, resulting in the detection of the respective deletions in the scaffolds as well as an inversion in TC06_scaffold_251445.

Cloning and Sanger-Sequencing of the RBA Gene from HN4 Genomic DNA and cDNA

Genomic DNA was extracted from the first true leaves of HN4 seedlings using he BioSprint 96 Plant kit on the BioSprint 96 Workstation (Qiagen) according to the manufacturer's protocol. Extracted DNA was quantified on the NanoDrop™ 8000 Spectrophotometer (Fisher Scientific) and normalized to 10 ng/μL.

Total RNA was extracted from HN4 stems harvested at anthesis and flash frozen liquid nitrogen using the Direct-Zol RNA miniprep kit (Zymo) according to the manufacturer's instructions. RNA concentration and purity were tested by NanoDrop (Thermo Fisher Scientific) and agarose gel electrophoresis. cDNA was synthesised using the SuperScript IV First-Strand cDNA Synthesis kit (Thermo Fisher Scientific) using Oligo d(T)20 primers, according to the manufacturer's instructions.

Full-length RBA gene sequences and coding sequences were amplified from HN4 genomic DNA and cDNA respectively using Q5 High-Fidelity DNA Polymerase (New England Biolabs). PCR reactions containing 1× Q5 High-Fidelity buffer, 2 mM dNTPs, 0.5 μM forward primer GAAGGGGTAGTGGAGTGGTAGTTG, 0.5 μM reverse primer GTGTTATACGATCATCGTTTTGC and 0.5 U Q5 DNA polymerase in a total volume of 25 μl were run on a Tetrad thermocycler (Bio-Rad) under the following conditions: 98° C. for 30 seconds, followed by 10 cycles of 98° C. for 10 seconds, 65° C. decreasing to 55° C. by 1° C. per cycle for 20 seconds, 72° C. for 1 minute, followed by 25 cycles of 98° C. for 10 seconds, 55° C. for 20 seconds, 72° C. for 1 minute, followed by 72° C. for 2 minutes, then a hold at 7° C. PCR products were checked on 1% agarose gel, extracted by Wizard SV PCR extraction kit (Promega) according to the manufacturer's instructions, and the concentration determined using the Qubit™ dsDNA BR Assay Kit (Thermo Fisher Scientific).

Purified RBA PCR product was cloned using the CloneJET PCR Cloning Kit (Thermo Fisher Scientific) according to the manufacturer's protocol and transformed into Subcloning Efficiency™ DH5a Competent Cells (Invitrogen) according to the manufacturer's protocol.

Between 2 and 12 single colonies positive for each insert were selected by colony PCR. Plasmids were extracted using the QIAprep Spin Miniprep kit (Qiagen) and used for Sanger-sequencing.

RNA Isolation for RNA Sequencing

Upper stem samples (defined as the 2 cm stem section immediately underneath the flower head) were collected from rba-1 and rba-2 mutant plants of the M4 generation as well as HN4 wild type at the time of anthesis. The samples were flash frozen in liquid nitrogen and stored at −80° C. until extraction. Grinding was performed in jars chilled in liquid nitrogen on the Qiagen TissueLyser as follows: 15 seconds at 20 Hz, followed by re-chilling in liquid nitrogen, then a further 15 seconds at 20 Hz. 100 mg of ground material was used per RNA extraction. RNA was isolated from the powder using a CTAB-based extraction method (Chang et al. (1993) Plant Mol. Biol. Rep. 11: 113-116) with small modifications: (i) three sequential extractions with chloroform:isoamylalcohol (24:1) were performed and (ii) the RNA was precipitated overnight with lithium chloride at −20° C. Following extraction the samples were treated with DNAse I using Ambion's DNA-free kit according to the manufacturers' protocol. After spectrophotometric quantification, equal amounts of RNA were pooled from three plants per mutant and HN4 wild type.

Library Preparation and RNA Sequencing

RNA sequencing library preparation was carried out by the Genomics Laboratory of the Bioscience Technology Facility of the Department of Biology, University of York. RNA quality was assessed by running 1 ul from each RNA pool on an Agilent Bioanalyzer RNA Nano chip. 900 ng good quality total RNA was then used per pool for mRNA sequencing library preparation using the NEB RNA Ultra Library preparation kit for Illumina in conjunction with the NEBNext Poly(A) mRNA Magnetic Isolation Module (New England BioLabs Inc.), and NEB Next single 6 bp indexing primers, according to the manufacturer's instructions. First, mRNA was purified from total RNA using two rounds of sample binding to oligo d(T)-coupled paramagnetic beads and washing. Purified mRNA was eluted from the beads into a first strand synthesis reaction buffer plus random primer mix, incubating at 94° C. for 12 minutes to fragment RNA. After addition of RNase inhibitors and ProtoScript II Reverse Transcriptase, first strand cDNA synthesis was performed by incubating at 10 minutes at 25° C., 50 minutes at 42° C. then 15 minutes at 70° C. Second strand synthesis and sample clean up were performed according to the manufacturer's guidelines, as were subsequent end preparation and adapter ligation steps. Libraries were amplified and complementary indices added in a 12 cycle PCR reaction. Following a final clean up step, the yield and size distribution of each amplified cDNA library was assessed using the Agilent High Sensitivity DNA kit with the Agilent 2100 Bioanalyzer and quantified using the Qubit with a HS dsDNA kit (Thermo Fisher Scientific). Libraries were then sent for 2×150 base paired end sequencing on a HiSeq 3000 at the University of Leeds Next Generation Sequencing Facility.

RNA Sequencing Analysis:

Three samples were sequenced, the number of reads were obtained as the following: rba-1, 2×28,154,370; rba-2, 2×21,681,680; and HN4 wild type,2×29,529,431. FASTQC method was used for QC analysis and Ribosomal RNA was filtered with mapping to rRNA_115_tax_silva_v1.0 downloaded from SILVA database (https://www.arb-silva.de/) using BOWTIE2 mapping software. The remaining RNA-seq reads were mapped to the reference transcript dataset of the 51,213 annotated proteins coding genes of the HN1 reference genome (ASM357369v1), using BWA mapping software with default parameters. Mapped reads were counted and retrieved using SAMTOOLS software package and the expression matrix were normalised to RPKM (Reads Per Kilobase of transcript, per Million mapped reads) values for subsequent comparative analyses.

Production of Stable Opium Poppy Transformants Constitutively Expressing RBA Under the Control of the CaMV 35S Promoter from Cauliflower Mosaic Virus The open reading frame of RBA was cloned into binary vector pRI 201-AN (Takara Bio Inc.) that includes a 5'-UTR untranslated region (5'UTR enhancer region) from the *Arabidopsis* alcohol dehydrogenase downstream of the CaMV 35S promoter to drive constitutive expression of candidate genes in plants.

Preparation of pRI 201-AN for Homology-Based Cloning

Plasmid pRI 201-AN was linearised by a double digest with SalI and NdeI (NEB) in rCutSmart™ buffer (NEB) for 1 hour at 37° C. according to the manufacturer's instructions. The digest was purified using the NucleoSpin™ Gel and PCR Clean-up kit (Macherey-Nagel™) according to the manufacturer's instructions to remove a small fragment from between the restriction sites.

Preparation of RBA ORF for Homology-Based Cloning

The open reading frame (ORF) of RBA was synthesised by GeneArt Gene Synthesis (Invitrogen/Thermo Fisher Scientific UK) and further amplified using PCRBIO HiFi Polymerase kit (PCRbiosystems) according to the manufacturer's instructions using primers 470 & 471 (Table 4), which contained 5'extensions to facilitate homology-based cloning into pRI 201-AN linearised with SalI and NdeI. PCR reactions were carried out in 5×20 μL reactions on a Thermocycler as follows: initial denaturing at 95° C. for 1 minute followed by 35 cycles of 95° C. for 15 seconds, 65° C. for 15 seconds and 72° C. for 30 seconds, followed by a final extension for 1 minute at 72° C. The PCR reactions were pooled and resolved on a 0.6% agarose gel. The PCR product of the expected size was cut out from the gel and purified using NucleoSpin™ Gel and PCR Clean-up kit (Macherey-Nagel™) according to the manufacturer's instructions. This purified RBA ORF PCR product was used for homology-based cloning into pRI 201-AN.

TABLE 4

Primers used to amplify the ORF of RBA for homology-based cloning into pRI 201-AN

| Primer_ ID | Notes | 5' extension | RBA specific sequence |
|---|---|---|---|
| 470 | RBA ORF reverse | agttgttga ttcagaattg | tcattcaatttg atcgaatgttc |
| 471 | RBA ORF forward | agttgttgat tcagaattg | atgatcagtagt tattctaagag |

Homology-Based Cloning of RBA into pRI 201-AN Linearised with SalI and NdeI

The pRI 201-AN_35 S::RBA expression construct (FIG. 3) was assembled from the purified RBA PCR product and the linearised pRI 201-AN vector using the Gibson Assembly® Cloning Kit (NEB) according the manufacturer's instructions. The correct integration of the RBA ORF and assembly of pRI 201-AN_35 S::RBA construct was sequence confirmed by Sanger-sequencing.

Preparation of Competent Cells of *Agrobacterium tumefaciens* Strain GV3101

*Agrobacterium tumefaciens* strain GV3101 cells were streaked out onto YEB plates containing Gentamicin (50 μg/ml) and Rifampicin (10 μg/ml) for antibiotic selection and grown at 28° C. with shaking for 2-3 days. A single colony was selected to inoculate a starter culture of 5 ml YEB liquid media with Gentamicin and Rifampicin selection. This was grown at 28° C. overnight, with shaking. The starter culture was used to inoculate a larger 100 ml culture with Gentamicin and Rifampicin selection that was grown for a further 3 hours at 28° C. with shaking to an $OD_{600}$ of 0.5-1.0. The culture was then chilled on ice for 10 mins before the cells were collected by centrifugation. The pelleted cells were resuspended in 2 ml of 20 mM $CaCl_2$) plus 10% glycerol and aliquoted prior to being immediately frozen in liquid nitrogen and stored at −80° C.

Transformation of *A. tumefaciens* Strain GV3101 with pRI 201-AN_35 S::RBA

One 50 μl aliquot of competent *A. tumefaciens* strain GV3101cells was defrosted on ice, and approximately 200 ng of the pRI 201-AN_35 S::RBA expression vector was added and swirled to mix. The cells were flash-frozen in liquid nitrogen, then defrosted at 37° C. in a water-bath for 5 minutes to heat shock followed by an incubation on ice for 30 minutes. Then, 250 μL of liquid LB medium was added, and the tube placed in a shaking incubator at 28° C. for 3 hours. The transformed cells were plated onto selective agar plates using Kanamycin (50 μg/ml) and Gentamicin (50 μg/ml) selection and incubated at 28° C. for 2 days to obtain single colonies.

A single colony was used to inoculate 5 ml LB plus Kanamycin and Gentamicin at 28° C. until dense culture was obtained to make a glycerol stock with 15% glycerol. Aliquots of the glycerol stocks were kept at −80° C.

Transformation of Opium Poppy with pRI 201-An_35 S::RBA

Wild type line HN4 and homozygous rba-1 deletion mutant material were used for stable transformation and expression of RBA using the pRI 201-An_35 S::RBA expression construct.

Seed Sterilisation

Prior to sowing poppy seeds were sterilised using a chlorine vapour method. A glass petri dish containing the seed was placed lid-off in a sealable box in the fume hood. The petri dish lid was also placed in the box along with a beaker containing a 3% hydrochloric acid solution. To release chlorine vapour, a 2.5 g Presept® Disinfectant Tablet (Johnson & Johnson) was added to the 3% hydrochloric acid solution and the box was sealed with parafilm and placed in a fume hood. After 90 minutes the seal was broken and the lid removed allowing the petri dish containing the sterilised seed to be carefully covered by the glass lid and removed from the sealable box to the laminar flow hood.

Seed Sowing

The sterilised seed was sown onto B50 agar medium in sterile tissue culture pots. B50 media composition is—B5 micro and macro elements (Duchefa Biochemie), B5 vitamins (Duchefa Biochemie), 20% sucrose, 2-(N-morpholino) ethanesulfonic acid (MES) buffer and 0.8% plant cell culture agar. The sown seed was stratified at 4° C. for 48 hours before being transferred to a growth cabinet to germinate and grow at 24° C. for 7-9 days.

Transformation of Hypocotyls Explants

*A. tumefaciens* pre-cultures were set up using glycerol stocks prepared from *A. tumefaciens* GV3101 cells containing the pRI 201-AN_35 S:RBA construct. A single 50 μl aliquot was added to 5 ml LB containing Kanamycin (50 μg/ml) and Gentamicin (50 μg/ml). The cultures were grown in a shaking incubator at 28° C. overnight. About 100 μl of the pre-culture was used to inoculate a 50 ml main culture of LB medium containing Kanamycin (50 μg/ml) and Gentamicin (50 μg/ml) which was grown in a shaking incubator at 28° C. overnight. Once an $OD_{600}$ of 0.3-0.8 was reached cells were harvested by centrifugation at 4000 rpm at 4° C. for 20 minutes. Inoculation culture was prepared by resuspending the cell pellet in inoculation medium to an $OD_{600}$ of between 0.2-0.3 and incubated for 1-3 hours at 28° C. on a shaker. The inoculation medium consisted of a liquid B50 medium without MES, but including Acetosyringone (100 μM).

Hypocotyl explants were carefully dissected from the roots and cotyledons of 7-9 day old poppy seedlings and immediately transferred into petri dishes containing the *Agrobacterium* inoculation culture. After gently shaking on an orbital shaker at room temperature for 15 minutes the explants were blotted on sterile filter paper to remove excess culture medium and transferred to solid co-cultivation medium for 2 to 3 days at 24° C. Co-cultivation medium consisted of the B50 medium plus agar with the addition of 2,4-Dichlorophenoxyacetic acid (1 μg/ml) and Acetosyringone (100 μM).

Inhibition of Agrobacteria and Selection of Transgenic Plants

After the co-cultivation period the explants were immersed in Timentin®-containing solution (150 μg/mL) in 50 mL Falcon tubes, agitated for 60 seconds and washed three times in sterile water. After blotting on sterile filter paper, explants were transferred to callus induction (CM) plates. CM medium consisted of B50 medium plus agar with Timentin® (150 μg/mL) and Paromomycin (30 μg/mL) in addition to 2,4-Dichlorophenoxyacetic acid (1 μg/ml). The CM plates were incubated in a growth cabinet at 24° C. Explants were transferred to fresh CM plates of the same composition at three-weekly intervals.

Production of Embryonic Callus Culture

Two types of calli formed on the explants (Chitty et al., 2003): Type I and Type II. Type I is a colourless loose callus that becomes brown over time. Type II forms as small regions of white compact embryogenic callus that appear after about 12 weeks on transformed explants.

Type II callus was removed from the explants and transferred to B50 media containing Timentin® (150 μg/mL) and Paromomycin (30 μg/mL) and incubated in a growth cabinet at 18-20° C. Type II calli were transferred to fresh B50 plates of the same composition at three-weekly intervals until somatic embryos started to form (typically after 2-3 culture periods).

Development of Somatic Embryos into Plantlets

Once plantlets were starting to develop from the somatic embryos, they were transferred to B50 medium with Timentin® (150 μg/mL) and Paromomycin (30 μg/mL) selection in baby jars to allow them to grow taller and to develop roots. Any basal callus as well as brown or dead leaves or shoots were removed before transfer.

Transfer of Plantlets to Soil

Plantlets with fully established root system were transferred to soil and initially kept in a humid environment and slowly hardened off by decreasing humidity over time. Once acclimatised to normal humidity levels the plants were transferred to plant growth cabinets or the glasshouse.

Empty Vector Control Transformants

Exactly the same procedure was followed to transform HN4 wild type and homozygous rba-1 deletion mutant material with pRI 201-AN empty vector, which is identical to the vector pRI 201-AN_35 S::RBA shown in FIG. 3 but lacked the RBA gene. Empty vector transformants served as control material.

Example 1

Discovery and Alkaloid Profiling of the Rba-1 and Rba-2 Mutant Alleles in the M2 Generation and Derived Materials A forward screen was carried out on the M2 generation of fast-neutron-mutagenized material of the HN4 variety. The screen was carried out in two rounds whereby in the first round latex of 12 week-old plants from the entire M2 mutant population was analysed by high throughput screening using Direct Injection MS without prior separation on the UPLC to monitor relative proportions of non-isobaric alkaloid groups. Any material showing latex phenotypes substantially different to HN4 control material where selected for the second round of screening by UPLC-MS against reference standards to obtain a full benzylisoquinoline alkaloid profile of the mature dry capsules.

Two independent M2 mutant plants belonging to different M2 seed families were identified in the latex screen as lacking any BIAs. The complete absence of measurable quantities of BIAs in these plants was confirmed by analysing mature dry M2 capsule material (Table 1). Following the characterisation of the molecular basis for the loss of BIAs in the mutant plants (Example 3 and 4) the mutant alleles were named 'regulator of benzylisoquinoline alkaloids-1' and '-2' (rba-1 and rba-2), respectively.

The rba-1 and rba-2 M2 mutant plants were self-pollinated and their respective progenies further propagated through several generations by self-pollinations to obtain a larger amount of material for testing the heritability and stability of the 'loss of all BIAs' phenotype.

As was the case for the M2 capsules, dry capsule material of the M3, M4 and M5 generations were devoid of the major alkaloids, morphine and noscapine, found in substantial amounts in the HN4 parental line. They also did not contain any other alkaloids in measurable quantities (Table 1). The analysis thus confirmed the 'loss of all BIAs' phenotype and showed that it is stably inherited.

The rba-1 mutant was crossed with two different morphine varieties, HM1 and HM8. Capsules of the F1 progeny, in which the rba-1 mutant allele is in the heterozygous state, did contain morphine and other morphinan alkaloids in similar amounts as the parental morphine varieties demonstrating that the rba-1 mutant allele is recessive (Table 1). Given that the rba-1 and rba-2 mutants carry different mutant alleles of the same genetic locus (Examples 3 and 4) the rba-2 allele can also be considered recessive.

A cross was carried out between the rba-1 and rba-2 mutants to test if they would complement each other with respect to BIA production. Since the HN4 wildtype phenotype was not rescued in capsules of the resulting F1 generation (Table 1) the rba-1 and rba-2 mutant alleles must belong to same complementation group with the respective mutations affecting same genetic locus. This was later confirmed by the characterisation of the molecular basis of the rba-1 and rba-2 mutants (Example 3).

TABLE 1

Alkaloid content in dry capsules of rba-1 and rba-2 mutant material and HN4 controls. Mature, dry capsules were analysed using UPLC-MS. Noted as ND (non-detectable) are concentrations below the background noise level, which is defined as the mean + 3 × the standard deviation (SD) of measurements from machine blank runs interspersed through each UPLC-MS analytical batch. For extremely low, near-zero concentrations where the SD was greater than the average measurement, the concentration was regarded as not significantly greater than zero and therefore noted as ND.

| | | | No. of | μg/mg (DW) | | | | | | | | | |
|---|---|---|---|---|---|---|---|---|---|---|---|---|---|
| | | Seed | plants | Morphine | | Oripavine | | Codeine | | Thebaine | | Noscapine | |
| Material | Generation | family | analysed | Mean | SD | Mean | SD | Mean | SD | Mean | SD | Mean | SD |
| HN4 | parental variety | | 11 | 5.59 | 1.97 | 0.00 | 0.00 | 0.31 | 0.15 | 0.02 | 0.01 | 5.51 | 1.71 |
| rba-1 | M2 | S-124620 | 1 | ND | | ND | | ND | | ND | | ND | |
| | M3 | S-185773 | 5 | ND | | ND | | ND | | ND | | ND | |
| | M4 | S-186036 | 6 | ND | | ND | | ND | | ND | | ND | |
| | | S-186056 | 8 | ND | | ND | | ND | | ND | | ND | |
| | | S-186099 | 4 | ND | | ND | | ND | | ND | | ND | |
| | | S-186809 | 3 | ND | | ND | | ND | | ND | | ND | |
| | | S-186810 | 2 | ND | | ND | | ND | | ND | | ND | |
| | M5 | S-187856 | 8 | ND | | ND | | ND | | ND | | ND | |
| | | S-189688 | 3 | ND | | ND | | ND | | ND | | ND | |
| rba-2 | M2 | S-124811 | 1 | ND | | ND | | ND | | ND | | ND | |
| | M3 | S-185766 | 4 | ND | | ND | | ND | | ND | | ND | |
| | M4 | S-186010 | 2 | ND | | ND | | ND | | ND | | ND | |
| | | S-186104 | 7 | ND | | ND | | ND | | ND | | ND | |
| | M5 | S-187863 | 6 | ND | | ND | | ND | | ND | | ND | |
| | | S-187864 | 5 | ND | | ND | | ND | | ND | | ND | |
| | | S-187867 | 5 | ND | | ND | | ND | | ND | | ND | |
| | | S-187869 | 6 | ND | | ND | | ND | | ND | | ND | |
| | | S-193333 | 7 | ND | | ND | | ND | | ND | | ND | |
| rba-1 × rba-2 | F1 | S-187882 | 13 | ND | | ND | | ND | | ND | | ND | |
| | | S-187883 | 9 | ND | | ND | | ND | | ND | | ND | |
| HM1 | morpine variety | | 7 | 14.03 | 3.62 | 0.07 | 0.05 | 1.06 | 0.48 | 0.76 | 0.30 | ND | |
| HM1 × rba-1 | F1 | S-189605 | 10 | 9.42 | 5.15 | 0.05 | 0.07 | 0.76 | 0.39 | 0.47 | 0.28 | 0.25 | 0.09 |
| HM8 | morpine variety | | 4 | 6.28 | 3.46 | 0.75 | 1.79 | 0.82 | 0.83 | 1.98 | 3.84 | 0.00 | 0.00 |
| HM8 × rba-1 | F1 | S-187901 | 3 | 16.70 | 6.01 | 0.03 | 0.02 | 1.53 | 0.56 | 0.60 | 0.35 | 0.33 | 0.23 |

Example 2

Transcriptome Analysis of Rbs-1 and Rbs-2 Mutant Material

To further characterise the mutants with respect to gene expressions levels of BIA biosynthesis genes, RNA sequencing was carried out on stem material of the M3 generation of the rba-1 and rba-2 as well as of the parental variety HN4. RPKM-normalised expression analysis revealed that compared to non-mutagenised HN4 wild type material the vast majority of BIA biosynthesis genes are strongly down-regulated in rba-1 and rba-2 mutant material compared to HN4 controls (Table 2). One example is NORCOCLAURINE SYNTHASE (NCS), which catalyses the first committed step in the biosynthesis of all BIAs in opium poppy (Samanani et al. (2004) Plant J. 40: 302-313). There are two NCS genes annotated in the opium poppy reference genome: PSUN64910.1 on scaffold ups_21 and PSUN03620.1 on scaffold ups_10. The RPKM-values of the rba-1 and rba-2 mutants are just 2 compared to 300 in the HN4 parental variety. Likewise, the respective RPKM-values of PSUN03620.1 are 8 and 2 in the rba-1 and -2 mutants compared to 130 in HN4.

TABLE 2

RNA sequencing gene expression analysis of alkaloid biosynthesis genes in stems of rba-1 and rba-2 mutants compared to the HN4 wild type. Upper stem tissue at anthesis was used for RNA isolation followed by RNAseq. RPKM-normalised expression levels are shown (RPKM = Reads per kilo base per million mapped reads). The column 'Gene ID' shows the opium poppy gene identifier from the annotation of the HN1 genome assembly (Guo et al. (2018) Sience. 362(6412): 343-347). Also shown are the public gene accession numbers as well as the scaffold of the HN1 reference assembly on which the respective genes reside.

| Gene name | | | | | Gene expression [RPKM] | | |
|---|---|---|---|---|---|---|---|
| (Accession number) | Gene Abbreviation | Gene description | Gene ID | Scaffold | HN4 Wild type | rba-1 mutant | rba-2 mutant |
| THS1 (AWQ63979.1) | THS | Thebaine synthase | PSUN63090.1 | ups_21 | 2340 | 20 | 17 |
| SALR (ABC47654.1) | SALR | Salutaridine reductase | PSUN63100.1 | ups_21 | 315 | 1 | 1 |
| SALAT (AAK73661.1) | SALAT | Salutaridinol 7-O-acetyltransferase | PSUN63110.1 | ups_21 | 77 | 0 | 0 |

TABLE 2-continued

RNA sequencing gene expression analysis of alkaloid biosynthesis genes in stems of rba-1 and rba-2 mutants compared to the HN4 wild type. Upper stem tissue at anthesis was used for RNA isolation followed by RNAseq. RPKM-normalised expression levels are shown (RPKM = Reads per kilo base per million mapped reads). The column 'Gene ID' shows the opium poppy gene identifier from the annotation of the HN1 genome assembly (Guo et al. (2018) Sience. 362(6412): 343-347). Also shown are the public gene accession numbers as well as the scaffold of the HN1 reference assembly on which the respective genes reside.

| Gene name | | | | | Gene expression [RPKM] | | |
|---|---|---|---|---|---|---|---|
| (Accession number) | Gene Abbreviation | Gene description | Gene ID | Scaffold | HN4 Wild type | rba-1 mutant | rba-2 mutant |
| SALSYN (ABR14720.1) | SALSYN (CYP719B1) | Salutaridine synthase | PSUN63120.1 | ups_21 | 470 | 4 | 0 |
| CODM (ADD85331.1) | CODM | Codeine O-demethylase gene copy | PS0135700.1 | chr1 | 80 | 52 | 17 |
| | | Codeine O-demethylase gene copy | PS0135710.1 | chr1 | 109 | 69 | 17 |
| | | Codeine O-demethylase gene copy | PS0135740.1 | chr1 | 107 | 65 | 15 |
| COR (AAF13736.1) | COR | Codeinone reductase gene copy | PS0700200.1 | chr7 | 86 | 47 | 20 |
| | | Codeinone reductase gene copy | PS0700850.1 | chr7 | 149 | 78 | 17 |
| T6ODM (ADD85329.1) | T6ODM | Thebaine 6-O-demethylase gene copy | PS0212910.1 | chr2 | 50 | 32 | 7 |
| | | Thebaine 6-O-demethylase gene copy | PS0212930.1 | chr2 | 53 | 32 | 6 |
| | | Thebaine 6-O-demethylase gene copy | PS0212950.1 | chr2 | 55 | 33 | 4 |
| | | Thebaine 6-O-demethylase gene copy | PS0212970.1 | chr2 | 62 | 41 | 8 |
| | | Thebaine 6-O-demethylase gene copy | PS0212980.1 | chr2 | 59 | 39 | 6 |
| SALR (ABC47654.1) | SALR | Salutaridine reductase | PS1126620.1 | chr11 | 626 | 19 | 22 |
| SALAT (AAK73661.1) | SALAT | Salutaridinol 7-O-acetyltransferase | PS1126610.1 | chr11 | 139 | 2 | 3 |
| SALSYN (ABR14720.1) | SALSYN (CYP719B1) | Salutaridine synthase | PS1126580.1 | chr11 | 324 | 66 | 28 |
| STORR (AKN63431.1) | STORR | (S)-to-(R)-reticuline P450-oxidoreductase | PS1126560.1 | chr11 | 483 | 74 | 25 |
| PSMT1 (AFB74611.1) | PSMT1 | O-methyltransferase 1 | PS1126480.1 | chr11 | 409 | 0 | 0 |
| CYP719A21 (AFB74615.1) | CYP719A21 | Canadine synthase | PS1126470.1 | chr11 | 587 | 0 | 1 |
| PSMT3 (AFB74613.1) | PSMT3 | O-methyltransferase 3 | PS1126440.1 | chr11 | 231 | 0 | 1 |
| CYP82Y1 (AFB74617.1) | CYP82Y1 | Cytochrome P450, CYP82Y1 | PS1126430.1 | chr11 | 175 | 5 | 4 |
| PSMT2 (AFB74612.1) | PSMT2 | O-methyltransferase 2 | PS1126420.1 | chr11 | 314 | 3 | 5 |
| PSAT1 (AFB74620.1) | PSAT1 | Acetyltransferase 1 | PS1126410.1 | chr11 | 167 | 1 | 0 |
| CYP82X2 (AFB74616.1) | CYP82X2 | Cytochrome P450, CYP82X2 | PS1126400.1 | chr11 | 179 | 9 | 13 |
| CYP82X1 (AFB74614.1) | CYP82X1 | Cytochrome P450, CYP82X1 | PS1126390.1 | chr11 | 186 | 2 | 2 |
| PSCXE1 (AFB74618.1) | PSCXE1 | Carboxylesterase 1 | PS1126380.1 | chr11 | 138 | 0 | 0 |
| PSSDR1 (AFB74619.1) | PSSDR1 | Short-chain dehydrogenase/ reductase | PS1126370.1 | chr11 | 440 | 43 | 8 |
| TNMT (AAY79177.1) | TNMT | (S)-tetrahydroprotoberberine-cis-N-methyltransferase | PS0702560.1 | chr7 | 112 | 1 | 3 |
| BBE (AAC61839.1) | BBE | Berberine bridge enzyme | PS1014490.1 | chr10 | 94 | 0 | 0 |

TABLE 2-continued

RNA sequencing gene expression analysis of alkaloid biosynthesis genes in stems of rba-1 and rba-2 mutants compared to the HN4 wild type. Upper stem tissue at anthesis was used for RNA isolation followed by RNAseq. RPKM-normalised expression levels are shown (RPKM = Reads per kilo base per million mapped reads). The column 'Gene ID' shows the opium poppy gene identifier from the annotation of the HN1 genome assembly (Guo et al. (2018) Sience. 362(6412): 343-347). Also shown are the public gene accession numbers as well as the scaffold of the HN1 reference assembly on which the respective genes reside.

| Gene name | | | | | Gene expression [RPKM] | | |
|---|---|---|---|---|---|---|---|
| (Accession number) | Gene Abbreviation | Gene description | Gene ID | Scaffold | HN4 Wild type | rba-1 mutant | rba-2 mutant |
| 4OMT2 (AAP45314.1) | 4OMT2 | 3'-hydroxy-N-methylcoclaurine 4'-O-methyltransferase 2 | PSUN64250.1 | ups_21 | 912 | 1 | 0 |
| 4OMT1 (AAP45313.1) | 4OMT1 | 3'-hydroxy-N-methylcoclaurine 4'-O-methyltransferase 1 | PSUN09500.1 | ups_107 | 79 | 0 | 0 |
| CYP80B1 (AAF61400.1) | CYP80B1 | (S)-N-methylcoclaurine 3'-hydroxylase | PS0533980.1 | chr5 | 63 | 18 | 8 |
| CNMT (AAP45316.1) | CNMT | Coclaurine N-methyltransferase | PS0701300.1 | chr7 | 216 | 0 | 0 |
| 6OMT (AAP45315.1) | 6OMT | Norcoclaurine 6-O-methyltransferase | PS0534030.1 | chr5 | 380 | 1 | 0 |
| NCS1 (AAX56303.1) | NCS | S-norcoclaurine synthase 1 | PSUN64910.1 | ups_21 | 300 | 2 | 2 |
| P6H (AGC92397.1) | P6H | Protopine 6-hydroxylase | PSUN20240.1 | ups_118 | 4 | 0 | 0 |
| N7OMT (ACN88562.1) | N7OMT | Norreticuline-7-O-methyltransferase | PSUN09470.1 | ups_107 | 128 | 0 | 0 |
| 4OMT2 (AAP45314.1) | 4OMT2 | 3'-hydroxy-N-methylcoclaurine 4'-O-methyltransferase 2 | PSUN02760.1 | ups_10 | 299 | 0 | 0 |
| 4OMT1 (AAP45313.1) | 4OMT1 | 3'-hydroxy-N-methylcoclaurine 4'-O-methyltransferase 1 | PS0700600.1 | chr7 | 385 | 0 | 1 |
| CYP80B1 (AAF61400.1) | CYP80B1 | (S)-N-methylcoclaurine 3'-hydroxylase | PSUN09510.1 | ups_107 | 6 | 0 | 0 |
| CNMT (AAP45316.1) | CNMT | Coclaurine N-methyltransferase | PS1023990.1 | chr10 | 337 | 0 | 0 |
| 6OMT (AAP45315.1) | 6OMT | Norcoclaurine 6-O-methyltransferase | PS0139160.1 | chr1 | 212 | 0 | 0 |
| NCS1 (AAX56303.1) | NCS | S-norcoclaurine synthase 1 | PSUN03620.1 | ups_10 | 130 | 8 | 2 |
| TNMT (AAY79177.1) | TNMT | (S)-tetrahydroprotoberberine-cis-N-methyltransferase | PS1020340.1 | chr10 | 289 | 3 | 6 |
| N7OMT (ACN88562.1) | N7OMT | Norreticuline-7-O-methyltransferase | PS0700580.1 | chr7 | 217 | 0 | 0 |
| N7OMT (ACN88562.1) | N7OMT | Norreticuline-7-O-methyltransferase | PS0700520.1 | chr7 | 167 | 0 | 0 |
| DIOX2 (ADD85330.1) | DIOX2 | Scoulerine O-demethylase | PSUN02990.1 | ups_10 | 24 | 11 | 2 |

Example 3

Determination of the Molecular Basis for of the 'Loss of all BIAs' Phenotype in the rba-1 and rba-2 Mutants To determine the molecular basis for the 'loss of all BIAs' phenotype, the genomes of rba-1 and rba-2 mutants were re-sequenced using the 10× Genomics platform and assembled inhouse using the Supernova software. The respective deletions in each mutant causing the 'loss of all BIAs' phenotype were identified using bioinformatic approaches as described in materials and methods.

With respect to the HN1 genome reference assembly 989 kb of genomic sequence on chromosome 9 containing 12 genes are deleted in the rba-1 mutant (FIG. 1, Table 3). In addition, 70 kb of genomic sequence immediately upstream of the 5' boundary of the deletion were found to be inverted.

In the rba-2 mutant, 780 kb of genomic sequence on chromosome 9 containing 11 genes were found to be deleted (FIG. 1, Table 3).

The fact the rba-1 and rba-2 deletion alleles identified in the respective mutants are unique in terms of their overall size and precise boundaries is consistent with them having arisen through independent mutation events in different M1 plants.

Consistent with the genetic complementation analysis (Example 1), the rba-1 and rba-2 deletion alleles overlap for 506 kb of genomic sequence (FIG. 1). This overlapping region deleted in both mutants contains 6 genes, one of which encodes a basic Helix-Loop-Helix (bHLH) transcription factor (Example 4).

Example 4

Corroboration of the Rba-1 and Rba-2 Deletion Mutations

The deletions identified in the rba-1 and rba-2 mutants by means of genome re-sequencing and assembly were further corroborated by gene expression analysis using the RNA sequencing data set from upper stems described above. The RPKM values of those genes residing in the respective deleted regions on chromosome 9 were compared between the rba-1 and rba-2 mutants and HN4 wild type (Table 3).

RPKM values of deleted genes would be expected to be low in the respective mutants compared to HN4 wild type—provided they expressed to reasonable levels in stem tissue of the HN4 wild type in the first place (RPKM values of deleted genes may not be absolutely zero in the respective mutants: low RPKM values may reflect background noise inherent to the methodology such as non-specific mapping of short reads from other genes with some degree of sequence similarity rather than genuinely low expression).

The RPKM values of the genes residing in the overlapping region deleted in both mutants are generally zero or low in both mutants compared to HN4 wild type. In contrast, RPKM-values of genes outside the overlapping region (and expressed to reasonable levels in HN4) show low expression only in the respective mutant in which they are deleted but not the other.

The RNA sequencing gene expression analysis thus confirms the respective deletions identified in the rba-1 and rba-2 genome assemblies as bona fide deletions.

Example 5

Discovery and Sequence Confirmation of the REGULATOR OF BENZYLISOQUINOLINE ALKALOIDS (RBA) Gene Of the six genes residing in the overlapping region deleted in both mutants only one shows homology with genes known to be involved in transcriptional regulation: PS0917990.1 encodes a bHLH transcription factor.

Since its deletion results in loss of expression of most genes known to be involved in BIA biosynthesis and, consequently, the 'loss of all BIAs' phenotype PS0917990.1 is a master regulator of BIA synthesis and accordingly named REGULATOR OF BENZYLISOQUINOLINE ALKALOIDS (RBA).

Cloning and Sanger-sequencing from genomic and cDNA confirmed the RBA sequence from HN4 to be identical to that from the HN1 reference genome assembly.

TABLE 3

RNAsequencing gene expression analysis of the genes residing in the genomic region of Chromosome 9 deleted in the rba-1 and rba-2 mutant lines
Upper stem tissue at anthesis was used for RNA isolation followed by RNAsequencing. RPKM-normalised expression levels are shown (RPKM = Reads per kilo base per million mapped reads). RPKM values obtained for rba-1 and rba-2 mutants are compared to the HN4 wild type. The column 'Gene ID' shows the opium poppy gene identifier from the annotation of the HN1 genome assembly. The column 'Deleted in' shows the mutant in which genome resequencing and assembly found the respective gene to be deleted. Genes PS0917890.1-PS0917930.1 are deleted in the rba-2 but not in the rba-1 mutant; genes PS0917940.1-PS0917990.1 reside in the overlapping region deleted in both mutants; genes PS0918000.1-PS0918050.1 are deleted in the rba-1 but not in rba-2 mutant. PS0917990.1 encodes the bHLH transcription factor RBA.

| | | | | | Gene expression [RPKM] | | |
|---|---|---|---|---|---|---|---|
| Gene abbreviation | Gene description | Gene ID | Deleted in | Scaffold | HN4 parental variety | rba-1 mutant | rba-2 mutant |
| | | PS0917890.1 | rba-2 | chr9 | 0 | 0 | 0 |
| | | PS0917900.1 | rba-2 | chr9 | 2 | 2 | 0 |
| | | PS0917910.1 | rba-2 | chr9 | 6 | 7 | 1 |
| | | PS0917920.1 | rba-2 | chr9 | 19 | 16 | 1 |
| | | PS0917930.1 | rba-2 | chr9 | 106 | 111 | 1 |
| | Ribosomal protein S5 | PS0917940.1 | rba-1 & rba-2 | chr9 | 10 | 2 | 8 |
| | tRNA-dihydrouridine synthase | PS0917950.1 | rba-1 & rba-2 | chr9 | 13 | 1 | 1 |
| | hypothetical protein | PS0917960.1 | rba-1 & rba-2 | chr9 | 23 | 3 | 3 |
| | hypothetical protein | PS0917970.1 | rba-1 & rba-2 | chr9 | 4 | 0 | 0 |
| | GPI transamidase component | PS0917980.1 | rba-1 & rba-2 | chr9 | 7 | 0 | 0 |
| RBA | REGULATOR OF BENZYLISOQUINOLINE ALKALOIDS | PS0917990.1 | rba-1 & rba-2 | chr9 | 27 | 0 | 0 |
| | hypothetical protein/aromatic aldehyde reductase | PS0918000.1 | rba-1 | chr9 | 6 | 0 | 6 |
| | | PS0918010.1 | rba-1 | chr9 | 45 | 5 | 53 |
| | | PS0918020.1 | rba-1 | chr9 | 21 | 0 | 33 |
| | | PS0918040.1 | rba-1 | chr9 | 5 | 1 | 1 |
| | | PS0918050.1 | rba-1 | chr9 | 1 | 0 | 3 |

The invention claimed is:

1. A *Papaver somniferum* plant, or plant part thereof, having reduced or undetectable activity of a transcription factor, wherein the sequence encoding said transcription factor comprises the nucleotide sequence set forth in SEQ ID NO:1, and wherein said nucleotide sequence is modified or deleted.

2. The *Papaver somniferum* plant, or plant part thereof, according to claim 1, wherein said nucleotide sequence is modified by deletion of at least one nucleotide base.

3. The *Papaver somniferum* plant, or plant part thereof, according to claim 1, wherein said nucleotide sequence is modified by deletion of all or part of the nucleotide sequence set forth in SEQ ID NO: 1.

4. The *Papaver somniferum*, or plant part thereof, according to claim 1, wherein said plant part thereof is a capsule.

5. The *Papaver somniferum* plant, or plant part thereof, according to claim 1, wherein said plant part thereof is a seed.

6. The *Papaver somniferum* plant, or plant part thereof, according to claim 1, wherein said *Papaver somniferum* plant, or plant part thereof, lacks benzylisoquinoline alkaloids or benzylisoquinoline precursors.

* * * * *